US007297340B2

(12) United States Patent
Apicella

(10) Patent No.: US 7,297,340 B2
(45) Date of Patent: Nov. 20, 2007

(54) VACCINE AND METHOD FOR PREVENTING BIOFILM FORMATION

(75) Inventor: Michael A. Apicella, Solon, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 371 days.

(21) Appl. No.: 10/753,980

(22) Filed: Jan. 7, 2004

(65) Prior Publication Data

US 2004/0202670 A1    Oct. 14, 2004

Related U.S. Application Data

(60) Provisional application No. 60/502,303, filed on Sep. 12, 2003, provisional application No. 60/438,600, filed on Jan. 7, 2003.

(51) Int. Cl.
*A61K 39/102* (2006.01)
(52) U.S. Cl. .................. 424/256.1; 424/235.1; 424/190.1; 435/252.3; 435/172.1
(58) Field of Classification Search ............. 424/256.1, 424/235.1, 90.1; 435/252.3, 172.1
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,873,192 A | 10/1989 | Kunkel | |
| 4,938,949 A | 7/1990 | Borch et al. | |
| 4,992,478 A | 2/1991 | Geria | |
| 5,336,490 A | 8/1994 | Brinton, Jr. et al. | |
| 6,743,607 B2 * | 6/2004 | Apicella et al. ............ | 435/101 |
| 7,109,294 B2 * | 9/2006 | O'Toole et al. ............ | 530/350 |

FOREIGN PATENT DOCUMENTS

| | | |
|---|---|---|
| WO | WO 01/30806 | 5/2001 |
| WO | WO 03/04689 | 1/2003 |

OTHER PUBLICATIONS

Altschul et al., "Basic Local Alignment Search Tool," *J. Mol. Biol.*, 1990, 215:403-410.
Altschul et al., "Gapped BLAST and PSI-BLAST: a new generation of protein database search programs," *Nucl. Acids. Res.*, 1997, 25(17):3389-3402.
Apicella et al., "Regulation and Biosynthesis of the Biofilm of Nontypeable *Haemophilus influenzae*," *Abstract of General Meeting of American Society for Microbiology*, 2003, 103:J21.
Bandi et al., "Nontypeable *Haemophilus influenzae* in the Lower Respiratory Tract of Patients with Chronic Bronchitis," *Am. J. Respir. Crit. Care Med.*, 2001, 164:2114-2119.
Barcak et al., "Two *Haemophilus influenzae* Rd Genes That Complement the *recA*-Like Mutation *rec*-1," *J. Bacteriol.*, 1989, 171(5):2451-2457.

Batzer et al., "Enhanced evolutionary PCR using oligonucleotides with inosine at the 3'-terminus," *Nucl. Acids. Res.*, 1991, 19(18):5081.
Bluestone, "Current Concepts in Otolaryngology. Otitis Media in Children: To Treat or Not to Treat?" *N. Engl. J. Med.*, 1982, 306(23):1399-1404.
Bouchet et al., "Host-derived sialic acid is incorporated into *Haemophilus influenzae* lipopolysaccharide and is a major virulence factor in experimental otitis media," *Proc. Natl. Acad. Sci. USA*, 2003, 100(15):8898-8903.
Burrows and Lam, "Effect of *wzx* (*rfbX*) Mutations on A-Band and B-Band Lipopolysaccharide Biosynthesis in *Pseudomonas aeruginosa* O5," *J. Bacteriol.*, 1999, 181(3):973-980.
Campagnari et al., "Antigenic Diversity of Lipooligosaccharides of Nontypable *Haemophilus influenzae*," *Infect. Immun.*, 1987, 55(4):882-887.
Corpet et al., "Multiple sequence alignment with hierarchical clustering," *Nucl. Acids Res.*, 1988, 16(2):10881-10890.
Costerton et al., "Bacterial Biofilms : A Common Cause of Persistent Infections," *Science*, 1999, 284:1318-1322.
Cox et al., "Identification and structural characterization of sialylated lacto-N-neotetraose structure in the lipopolysaccharide of *Haemophilus influenza*," *Eur. J. Biochem.*, 2002, 269:4009-4019.
Davies and Geesey, "Regulation of the Alginate Biosynthesis Gene *algC* in *Pseudomonas aeruginosa* during Biofilm Development in Continuous Culture," *Appl. Environ. Microbiol.*, 1995, 61(3):860-867.
Davies et al., "Exopolysaccharide Production in Biofilms: Substratum Activation of Alginate Gene Expression by *Pseudomonas aeruginosa*," *Appl. Environ. Microbiol.*, 1993, 59(4):1181-1186.
Edwards et al., "*Neisseria gonorrhoeae* Elicits Membrane Ruffling and Cytoskeletal Rearrangements Upon Infection of Primary Human Endocervical and Ectocervical Cells," *Infect. Immun.*, 2000, 68(9):5354-5363.
Ehrlich et al., "Mucosal Biofilm Formation on Middle-Ear Mucosa in the Chinchilla Model of Otitis Media," *JAMA*, 2002, 287(13):1710-1715.
Fleischmann et al., "Whole-Genome Random Sequencing and Assembly of *Haemophilus influenzae* Rd," *Science*, 1995, 269:496-512.
Gaucher et al., "Mass Spectral Characterization of Lipooligosaccharides from *Haemophilus influenzae* 2019," *Biochemistry*, 2000, 39:12406-12414.
Gibson et al., "Characterization of Bacterial Lipooligosaccharides by Delayed Extraction Matrix- Assisted Laser Desorption Ionization Time-of-Flight Mass Spectrometry," *J. Am. Soc. Mass Spectrom.*, 1997, 8:645-658.
Hall-Stoodley and Stoodley, "Developmental regulation of microbial biofilms," *Curr. Opin. Biotechnol.*, 2002, 13:228-233.

(Continued)

*Primary Examiner*—Jennifer E. Graser
(74) *Attorney, Agent, or Firm*—Viksnins Harris & Padys PLLP

(57) ABSTRACT

The present invention is directed to compounds and methods for immunizing a patient against a biofilm-producing bacterial infection and a vaccine related thereto.

5 Claims, 18 Drawing Sheets

OTHER PUBLICATIONS

Heydorn et al., "Quantification of biofilm structures by the novel computer program COMSTAT," *Microbiology*, 2000, 146:2395-2407.

Higgins et al., "Fast and sensitive multiple sequence alignments on a microcomputer," *CABIOS*, 1989, 5:151-153.

Higgins et al., "CLUSTAL: a package for performing multiple sequence alignment on a microcomputer," *Gene*, 1988, 73:237-244.

Hitchcock and Brown, "Morphological Heterogeneity Among *Salmonella* Lipopolysaccharide Chemotypes in Silver-Stained Polyacrylamide Gels," *J. Bacteriol.*, 1983, 154:269-277.

Hood et al., "Sialic acid in the lipopolysaccharide of *Haemophilus influenzae*: strain distribution influence on serum resistance and structural characterization," *Mol. Microbiol.*, 1999, 33(4):679-692.

Hood et al., "Identification of a lipopolysaccharide α-2,3-sialyltransferase from *Haemophilus influenzae*," *Mol. Microbiol.*, 2001, 39(2):341-350.

Hood et al., "Use of the complete genome sequence information of *Haemophilus influenzae* strain Rd to investigate lipopolysaccharide biosynthesis," *Mol. Microbiol.*, 1996, 22(5):951-965.

Huang et al., "Parallelization of a local similarity algorithm," *CABIOS*, 1992, 8(2):155-165.

Jackson et al., "Biofilm Formation and Dispersal under the Influence of the Global Regulator CsrA of *Escherichia coli*," *J. Bacteriol.*, 2002, 184(1):290-301.

Jones et al., "*Haemophilus influenzae* Type b Strain A2 Has Multiple Sialyltransferases Involved in Lipooligosaccharide Sialylation," *J. Biol. Chem.*, 2002, 277(17):14598-14611.

Karlin and Altschul, "Applications and statistics for multiple high-scoring segments in molecular sequences," *Proc. Natl. Acad. Sci. USA*, 1993, 90:5873-5877.

Karlin and Altschul, "Methods for assessing the statistical significance of molecular sequence features by using general scoring schemes," *Proc. Natl. Acad. Sci. USA*, 1990, 87:2264-2268.

Keenleyside et al., "A plasmid-encoded $rfb_{O:54}$ gene cluster is required for biosynthesis of the O:54 antigen in *Salmonella enterica* serovar Borreze," *Mol. Microbiol.*, 1994, 11(3):437-448.

Kirkham and Murphy, "Biofilm Formation by Nontypeable *Haemophilus influenzae*: Strain Variability, Outer Membrane Antigen Expression and Role of Pili," *Abstracts of General Meeting of American Society for Microbiology*, 2002, 102:172.

Kirkham and Murphy, "Expression of a 30kDa Peroxiredoxin Protein in Biofilms and During Human Respiratory Tract Infection by *Haemophilus influenzae*," *Abstracts of General Meeting of American Society for Microbiology*, 2003, 103:D259.

Kunkel et al., "Rapid and Efficient Site-Specific Mutagenesis without Phenotypic Selection," *Meth. Enzymol.*, 1987, 154:367-382.

Kunkel, "Rapid and efficient site-specific mutagenesis without phenotypic selection," *Proc. Natl. Acad. Sci. USA*, 1985, 82:488-492.

Lee et al., "Detachment of *Streptococcus mutans* Biofilm Cells by an Endogenous Enzymatic Activity," *Infect. Immun.*, 1996, 64(3):1035-1038.

Månsson et al., "A new structral type for *Haemophilus influenzae* lipoplysaccharide. Structral analysis of the lipopolysaccharide from nontypeable *Haemophilus influenzae* strain 486," *Eur. J. Biochem.*, 2001, 268:2148-2159.

Månsson et al., "Structural analysis of the lipopolysaccharide from nontypeable *Haemophilus influenzae* strain 1003," *Eur. J. Biochem.*, 2002, 269:808-818.

Maskell et al., "The gal locus from *Haemophilus influenzae*: cloning, sequencing and the use of gal mutants to study lipopolylsaccharide," *Mol. Microbiol.*, 1992, 6(20):3051-3063.

Masoud et al., "Structure of the Variable and Conserved Lipopolysaccharide Oligosaccharide Epitopes Expressed by *Haemophilus influenzae* Serotype b Strain Eagan," *Biochemistry*, 1997, 36:2091-2103.

McGhee et al., "New Perspectives in Mucosal Immunity With Emphasis on Vaccine Development," *Sem. Hematol.*, 1993, 30(4):3-15.

McLaughlin et al., "Generation of Lipooligosaccharide Mutants of *Haemophilus influenzae* Type b," *J. Bacteriol.*, 1992, 174(20):6455-6459.

Meier-Dieter et al., "Biosynthesis of Enterobacterial Common Antigen in *Escherichia coli*," *J. Biol. Chem.*, 1990, 265:13490-13497.

Meier-Dieter et al., "Nucleotide Sequences of the *Escherichia coli rfe* Gene Involved in the Synthesis of Enterobacterial Common Antigen," *J. Biol. Chem.*, 1992, 267:746-753.

Meinkoth and Wahl, "Hybridization of Nucleic Acids Immobilized on Solid Supports," *Anal. Biochem.*, 1984, 138:267-284.

Miller and Bassler, "Quorum Sensing in Bacteria," *Annu. Rev. Microbiol.*, 2001, 55:165-199.

Morse et al., "Effect of Dilution Rate on Lipopolysaccharide and Serum Resistance of *Neisseria gonorrhoeae* Grown in Continuous Culture," *Infect. Immun.*, 1983, 41(1):74-82.

Murphy and Apicella, "Nontypable *Haemophilus influenzae*: A Review of Clinical Aspects, Surface Antigens, and the Human Immune Response to Infection," *Rev. Infect. Dis.*, 1987, 9:1-15.

Murphy and Kirkham, "Biofilm formation by nontypeable *Haemophilus influenzae*: strain variability, outer membrane antigen expression and role of pili," *BMC Microbiol.*, 2002, 2:7-14.

Myers and Miller, "Optimal alignments in linear space," *CABIOS*, 1988, 4:11-17.

Needleman and Wunsch, "A General Method Applicable to the Search for Similarities in the Amino Acid Sequence of Two Proteins," *J. Mol. Biol.*, 1970, 48:443-453.

Ohta et al., "Cloning and expression of the *rfe-rff* gene cluster of *Escherichia coli*," *Mol. Microbiol.*, 1991, 5:1853-1862.

Ohtsuka et al., "An Alternative Approach to Deoxyoligonucleotides as Hybridization Probes by Insertion of Deoxyinosine at Ambiguous Codon Positions," *J. Biol. Chem.*, 1985, 260(5):2605-2608.

O'Toole and Kolter, "Initiation of biofilm formation in *Pseudomonas fluorescens* WCS365 proceeds via multiple, convergent signaling pathways: a genetic analysis," *Mol. Microbiol.*, 1998, 28(3):449-461.

O'Toole and Kolter, "Flagellar and twitching motility are necessary for *Pseudomonas aeruginosa* biofilm development," *Mol. Microbiol.*, 1998, 30(2):295-304.

Pearson and Lipman, "Improved tools for biological sequence comparison," *Proc. Natl. Acad. Sci. USA*, 1988, 85:2444-2448.

Pearson, "Using the FASTA Program to Search Protein and DNA Sequence Databases," *Meth. Mol. Biol.*, 1994, 24:307-489.

Phillips et al., "Structural Characterization of the Cell Surface Lipooligosaccharides from a Nontypable Strain of *Haemophilus influenzae*," *Biochemistry*, 1992, 31:4515-4526.

Phillips et al., "Structural Studies of the Lipooligosaccharides from *Haemophilus influenzae* Type b Strain A2," *Biochemistry*, 1993, 32:2003-2012.

Phillips et al., "Characterization of Two Transposon Mutants from *Haemophilus influenzae* Type b with Altered Lipooligosaccharide Biosynthesis," *Biochemistry*, 1996, 35:5937-5947.

Phillips et al., "Characterization of Chimeric Lipopolysaccharides from *Escherichia coli* Strain JM109 Transformed with Lipooligosaccharide Synthesis Genes (*lsg*) from *Haemophilus influenzae*," *J. Biol. Chem.*, 2000, 275:4747-4758.

Puskas et al., "A Quorum-Sensing System in the Free-Living Photosynthetic Bacterium *Rhodobacter sphaeroides*," *J. Bacteriol.*, 1997, 179:7530-7537.

Rossolini et al., "Use of deoxyinosine-containing primers vs degenerate primers for polymerase chain reaction based on ambiguous sequence information," *Mol. Cell. Probes*, 1994, 8:91-98.

Sauer et al., "*Pseudomonas aeruginosa* Displays Multiple Phenotypes during Development as a Biofilm," *J. Bacteriol.*, 2002, 184:1140-1154.

Schweda et al., "Structural studies of the saccharide part of the cell envelope lipopolysaccharide from *Haemophilus influenzae* strain AH1-3 (*lic3* + )," *Carbohydr. Res.*, 1993, 246:319-330.

Schweda et al., "Structural analysis of lipopolysaccharide oligosaccharide epitopes expressed by non-typeable *Haemophilus influenzae* strain 176," *Carbohydr. Res.*, 2002, 337:409-420.

Schweda et al., "Characterization of the phosphocholine-substituted oligosaccharide in lipopolysaccharides of type b *Haemophious influenzae*," *Eur. J. Biochem.*, 2000, 267:3902-3913.

Shibata et al., "Expression and Characterization of Streptococcal *rgp* Genes Required for Rhamnan Synthesis in *Escherichia coli*," *Infect. Immun.*, 2002, 70:2891-2898.

Shibuya et al., "The Elderberry (*Sambucus nigra* L.) Bark Lectin Recognizes the Neu5Ac(α2-6)Gal/GalNAc Sequence," *J. Biol. Chem.*, 1987, 262:1596-1601.

Singh et al., "Quorum-sensing signals indicate that cystic fibrosis lungs are infected with bacterial biofilms," *Nature*, 2000, 407:762-764.

Singh et al., "A component of innate immunity prevents bacterial biofilm development," *Nature*, 2002, 417:552-555.

Smith et al., "Comparison of Biosequences," *Adv. Appl. Math.*, 1981, 2:482-489.

Stoodley et al., "Biofilms as Complex Differentiated Communities," *Annu. Rev. Microbiol.*, 2002, 56:187-209.

Swords et al., "Non-typeable *Haemophilus influenzae* adhere to and invade human bronchial epithelial cells via an interaction of lipooligosaccharide with the PAF receptor," *Mol. Microbiol.*, 2000, 37:13-27.

Tolker-Nielsen et al., "Development and Dynamics of *Pseudomonas* sp. Biofilms," *J. Bacteriol.*, 2000, 182:6482-6489.

Turner et al., "The Potential Exploitation of Plant Viral Translational Enhancers in Biotechnology for Increased Gene Expression," *Mol. Biotech.* 1995, 3:225-236.

Wang and Cummimgs, "The Immobilized Leukoagglutinin from the Seeds of *Maackia amurensis* Binds with High Affinity to Complex-type Asn-linked Oligosaccharides Containing Terminal Sialic Acid-linked α-2,3 to Penultimate Galactose Residues," *J. Biol. Chem.*, 1988, 263:4576-4585.

Whiteley et al., "Gene expression in *Pseudomonas aeruginosa* biofilms," *Nature*, 2001, 413:860-864.

Williams et al., "Cell transfer by filtration: evaluation of protocols for transformational competence," *FEMS Microbiol. Lett.*, 1996, 137:183-187.

\* cited by examiner

```
         10         20         30         40         50         60
          |          |          |          |          |          |
MKNTEILLTI KLQQALFIDP KRVRLLKEIQ QCGSINQAAK NAKVSYKSAW DHLEAMNKI 70         80         90        100        110        120
          |          |          |          |          |          |
PRPLLERNTG GKNGGGTALT TYAERLLQLY DLLERTQEHA FHILQDESVP LDSRLTATA 130        140        150        160        170        180
          |          |          |          |          |          |
FSLQSSARNQ FFGRVAQQRI IDSRCVVDVN VQGLPTPLQV SITTKSSARL KLITEKEVM 190        200        210        220        230        240
          |          |          |          |          |          |
MFKAPWVKIS EQPLANQPNQ FPVNIKSLNE EEAILQFAES NIEFCATVHQ PNQWQIEQQ

250
          |
WIHIDQEQII LATLG
```

FIG. 2A

```
ATGAAAAAACACCGAAATTTACTCACCATTAAACTTCAACAAGCACTTTATCGATCCA
AAACGAGTTCGTTACTCAAAGAAATTCAACAATGCGGTTCAATTAATCAAGCTGCGAAA
AATGCCAAAGTGAGCTATAAAAGTGCGTGGGATCATTAGAAGCCATGAATAAATCAGC
CCTCGCCCATTGCTGGAACGAAATACAGGTGAAAAAATGGCGGACACGGCACTTACT
ACTTATGCCGAGCGTTGCTCCAACTTTATGATTTATTAGAACGTACGCAAGAACACGCG
TTTCATATTCTACAAGATGAATCCGTACCGTTAGATAGTTTACTCACGCAACCGCACGT
TTTTCTTTACAAAGTAGCGCACGCAATCAATTTTTGGGCGAGTGGCACACAACGCATT
ATTGACTCTCGTTGCGTTGTGATGTGAATGTGCAAGGATTACCAACGCCATTGCAAGTT
TCTATTACCACAAAGCTCGGCTCGTTGAAACTCATTACGGAAAAGAAGTGATGCTG
ATGTTCAAGGCTCCTTGGGTAAAAATCACTCAATGAACAACCATTAGCAAATCAACGAATCAG
TTCCCCGTAAATATCAAATCACTCAATGAAGAGAAGCCATCCTTCAATTGCTGAAAGC
AACATTGAATTTGTGCCACAGTCCACCAGCAAATCAATGGCAAATCGAGCAACAGGTT
TGGATTCACATTGATCAAGGAGCAAATTATTTTAGCGACGCTGGGG
```

FIG. 2B

```
         10         20         30         40         50         60
          |          |          |          |          |          |
MLSIFVTFLG AFLTLIVMRP LANWIGLVDK PNYRKRHQGT IPLIGGASLF VGNLCYYLM 70         80         90        100        110        120
          |          |          |          |          |          |
WDQLRLPYLY LFSIFVLLAI GILDDRFDIS PFLRAGIQAI LAILMIDLGN IYLDHLGQI 130        140        150        160        170        180
          |          |          |          |          |          |
GPFQLTLGSI GLIITVFATI AIINAFNMID GIDGLLGGLS CVSFAAIGIL MYRDGQMDM 190        200        210        220        230        240
          |          |          |          |          |          |
HWSFALIVSI LPYLMLNLGI PFGPKYKVFM GDAGSTLIGF TIIWILLST QGKGHPMNP 250        260        270        280        290        300
          |          |          |          |          |          |
TALWIIAIPL IDMVAIIYRR VRKGKSPFRP DRLHVHHLMV RAGLTSRQAF LLITFVSAV 310        320        330        340        350
          |          |          |          |          |
ATIGILGEVY YVNEWAMFVG FFILFFLYVY SITHAWRITR WVRRMKRRAK RLKKA
```

FIG. 4A

```
ATGCTGAGTATTTTGTTACTTTTCTTGGCGCGTTTTAACATTGATTGTGATGCGACCA
CTTGCCAATTGGATTGGATTAGTCGATAAACTATCGTAAACGTCATCAAGGCACA
ATTCCACTAATCGGTGGCGCATCGCTTTTGTGGTAATCTTGCTATTATCTGATGGAA
TGGGATCAACTTCGATTACCGTATCTTTATTGTTCAGTATTTTGTTTTATTGGCGATT
GGGATTTAGATGATCGCTTTGATATTAGCCCCTTTTTTAAGAGCAGGCATTCAAGCAATA
TTGGCGATTTTAATGATCTTGGGAATATTTATCTTGATTATTACCGTCTTTGCCACTATT
GGGCCTTTCCAATTAACGCTTTAATGATTGATGTATTGATTGCTTGGGGACTCTCT
GCGATTATTAATGCCTTTGCGGCGATTGGTATTTTAATGTATCGAGATGGGCAAATGGATATGGCG
TGTGTTCTTTTGCGGCGATTGGTATTTTAATGTATCGAGATGGGCAAATGGATATGGCG
CATTGGAGTTTTGCTCTTTAATCGTATAAGGTGTTTATTGCCCGGGATGCCGGGAGTACATCCTAATTGGCTTT
CCATTATTGGACCAAAATATAAGTTTGTTATTAAGTACGCAAGGAAAAGGGCATCCTATGAATCCAGTA
ACCATTATTGGATTTGTTATTAAGTACGCAAGGAAAAGGGCATCCTATGAATCCAGTA
ACCGCACTTTGGATTATTGCGATTCCTTTGATTGATATGGTTGCGATTATTATCGCCGT
GTACGTAAAGGTAAACGCCCATTCCAGATGTTCATGTTCATCATTAATGGTA
AGAGCGGGTTTAACATCAAGACAAGCCTTTTATTATTGATTACGTTTGTTTCTGCAGTTGT
GCAACTATCGGTATTTTCCTTTATGTCTATTCAATTACGCATGAATGAGTGGCGATGTTTGTTGGC
TTTTCATTTATTTTTTTCCAAACGTCGTGCCAAACGGTTGAAGAAAGCA
TGGGTAAGAAGAATGAAACGGTTGAAGAAAGCA
```

FIG. 4B

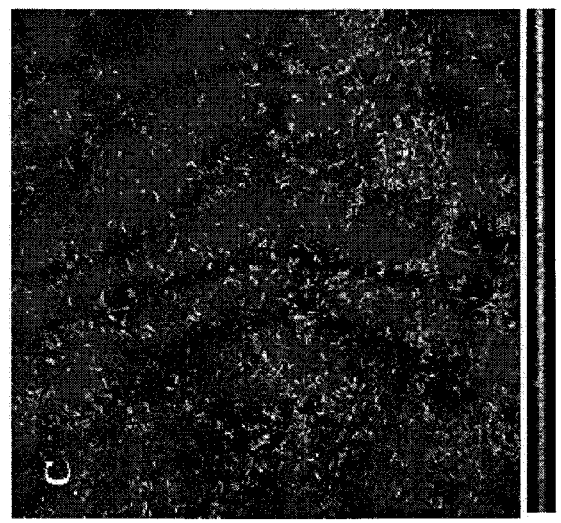
FIG. 9A
FIG. 9B
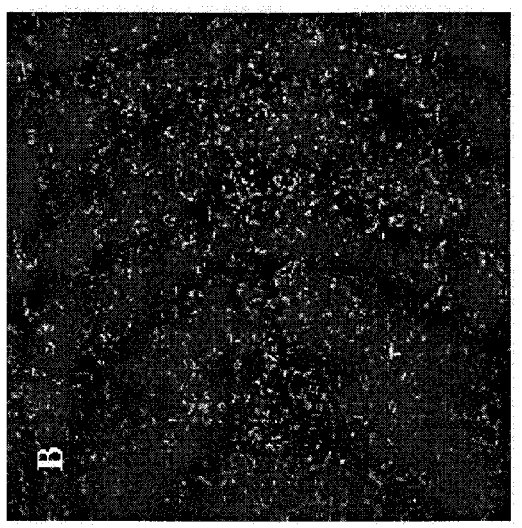
FIG. 8A
FIG. 8B
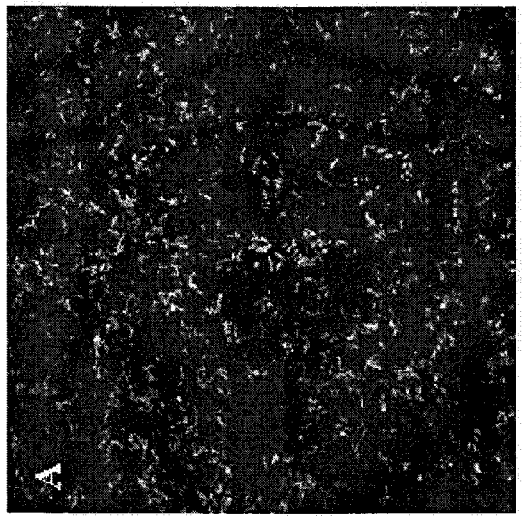
FIG. 7A
FIG. 7B

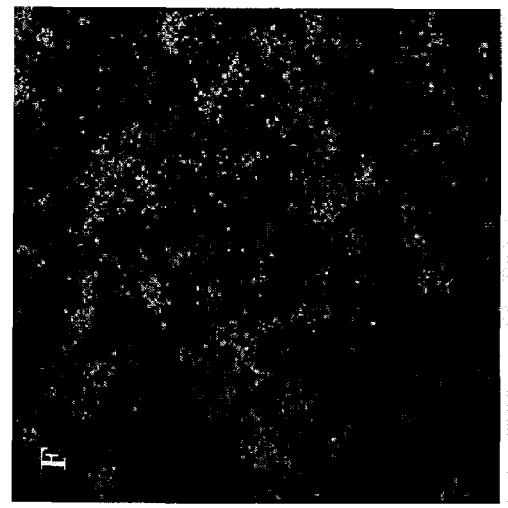
FIG. 12A  FIG. 12B
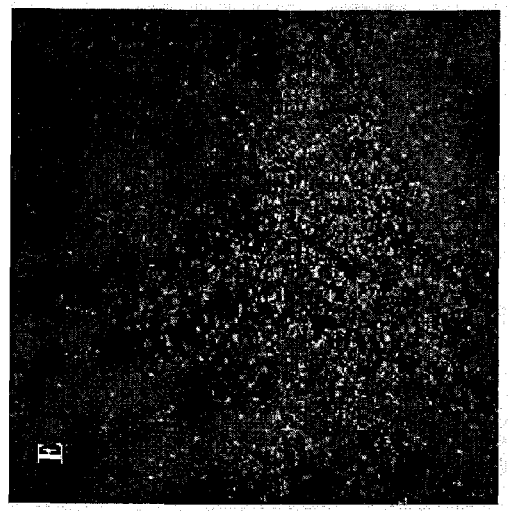
FIG. 11A  FIG. 11B
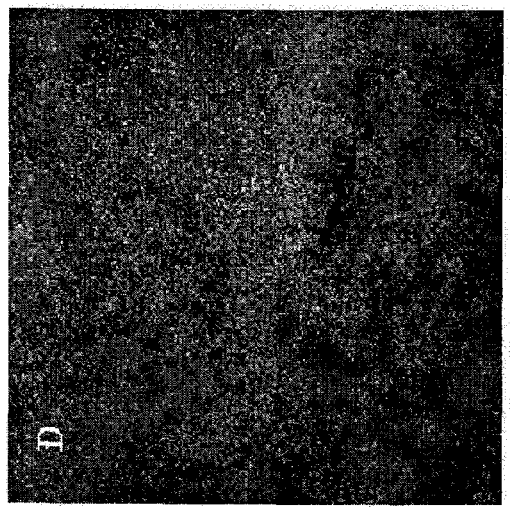
FIG. 10A  FIG. 10B

VACCINE AND METHOD FOR PREVENTING BIOFILM FORMATION

CROSS-REFERENCE TO RELATED APPLICATIONS

This application claims priority to U.S. Provisional Application No. 60/438,600, filed Jan. 7, 2003, and U.S. Provisional Application No. 60/502,303, filed Sep. 12, 2003, which applications are incorporated herein by reference.

U.S. GOVERNMENT RIGHTS

This work was supported by the United States Public Health Service NIAID, National Institutes of Health, Grants AI24616 and AI30040. The United States Government may have certain rights to this invention.

BACKGROUND OF THE INVENTION

Over the past ten years, studies have shown that biofilm formation by bacteria is a factor in their ability to survive on artificial and mucosal surfaces. Recent studies have indicated that nontypeable *Haemophilus influenzae* (NTHi) produces biofilms during middle ear infection in animal models. Bacteria growing as a biofilm display a different phenotype than free-living bacteria. They have greatly reduced metabolic rates that render them nearly impervious to antimicrobial treatment, and they have an exopolysaccharide matrix that provides protection from phagocytosis and other host defense mechanisms. They also demonstrate reliance on complex intercellular communication systems that provide for organized growth characteristics. Further, they are recalcitrant to standard culture techniques because of their altered metabolism.

The reduced metabolic and divisional rates of biofilm bacteria largely explain the failure of antibiotics to eliminate infections in patients who have biofilm-colonized indwelling medical devices, primarily because non-dividing bacteria largely escape antibiotic killing. Antibiotic treatment of biofilms kills bacteria on the periphery, but deep organisms persist and act as a nidus for regrowth and periodic planktonic (i.e., "free-floating" bacterial) showers, that can result in systemic infection.

There exists a need in the art for a method to treating infections associated with biofilm-producing bacteria.

SUMMARY OF THE INVENTION

Recent evidence indicates that biofilm formation occurs in otitis media (OM) and is an important mechanism by which nontypeable *Haemophilus influenzae* (NTHi) causes this disease. As described herein, it has been discovered that *H. influenzae* 2019 lsgG and 2019 rfe are involved in NTHi biofilm formation, and that mutation of these genes prevents biofilm formation. The induction of antibodies by NTHi LsgG and Rfe vaccines inactivate these proteins and prevent biofilm formation.

The present invention provides a vaccine comprising an immunogenic amount of a biofilm peptide, which amount is effective to immunize a patient against a biofilm-producing bacterial infection, for example, a *Haemophilus influenzae* infection, in combination with a physiologically-acceptable, non-toxic vehicle. In one embodiment of the invention, the vaccine comprises a biofilm peptide from a *Haemophilus influenzae*. As used herein, the term "biofilm peptide" includes variants or biologically active or inactive fragments of this polypeptide. A "variant" of the polypeptide is a biofilm peptide that is not completely identical to a native biofilm peptide. A variant biofilm peptide can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. In one embodiment, the biofilm peptide is a LsgG gene product and/or a Rfe gene product. The infection can be a chronic infection. The infection can be caused by a bacterial-biofilm. The infection can be otitis media (OM), otitis media with effusion (OME), or chronic bronchitis.

The present invention also provides a method of treating or preventing a *Haemophilus influenzae* infection, comprising administering to a patient such a vaccine.

The present invention additionally provides a method of preventing infection or colonization of *Haemophilus influenzae* in a patient by administering to the patient an agent that inhibits the production of a *Haemophilus influenzae* biofilm peptide.

In addition, the present invention provides an isolated and purified *Haemophilus influenzae* cell comprising a disrupted biofilm gene, for example, LsgG or Rfe, of the cell, wherein the disruption results in a reduction of biofilm formation in the transgenic *Haemophilus influenzae* cell as compared to a wild-type *Haemophilus influenzae* cell. In one embodiment, the biofilm gene can is disrupted by insertional inactivation.

BRIEF DESCRIPTION OF THE FIGURES

FIG. 2A depicts *Haemophilus influenzae* LsgG amino acid sequence (SEQ ID NO:1), the assigned homology of which is molybdenum regulatory protein (modE), and FIG. 2B depicts *Haemophilus influenzae* LsgG nucleic acid sequence (SEQ ID NO:2).

FIG. 4A depicts *Haemophilus influenzae* Rfe amino acid sequence (SEQ ID NO:3), the assigned homology of which is undecaprenyl-phosphate alpha-N-acetylglucosaminyl-transferase (rfe), and FIG. 2B depicts *Haemophilus influenzae* Rfe nucleic acid sequence (SEQ ID NO:4).

FIG. 6A shows a schematic representation of the flow chamber. The top surface is a glass cover slip (doffed lines) to which the biofilm adheres. This is sealed to the chamber with silicone cement. The chamber is infected with either $10^7$ NTHi 2019 gfp, NTHi 2019lsgG gfp or NTHi 2019rfe gfp. A continuous flow of defined medium essential medium diluted 1:10 is flowed through the chamber at 180 microliters per minute. The development biofilms is monitored by confocal microscopy every 24 hours for 4 to seven days. FIG. 6B shows a chamber infected with NTHi 2019.

FIGS. 7A and 7B show the confocal examination of flow chamber studies of strain NTHi 2019::gfp at day one (7A and 7B). FIG. 7B represents a vertical cross-section of the Z-series shown in FIG. 7A. As can be seen, a biofilm with a vertical height of approximately 15 microns forms over a 4 day NTHi 2019 infection while minimal to no biofilm forms during a similar period of infection with strains NTHi 2019rfe::gfp (FIGS. 11A and 11B) or NTHi 2019lsgG::gfp (FIGS. 12A and 12B).

FIGS. 8A and 8B show the confocal examination of flow chamber studies of strain NTHi 2019rfe::gfp at day one (8A and 8B). FIG. 8B represents a vertical cross-section of the Z-series shown in FIG. 8A.

FIGS. 9A and 9B show the confocal examination of flow chamber studies of strain NTHi 2019lsgG::gfp at day one (9A and 9B). FIG. 9B represents a vertical cross-section of the Z-series shown in FIG. 9A.

FIGS. 10A and 10B show the confocal examination of flow chamber studies of strain NTHi 2019::gfp at day four (10A and 10B). FIG. 10B represents a vertical cross-section of the Z-series shown in FIG. 10A.

FIGS. 11A and 11B show the confocal examination of flow chamber studies of strain NTHi 2019rfe::gfp at day four (11A and 11B). FIG. 11B represents a vertical cross-section of the Z-series shown in FIG. 11A.

FIGS. 12A and 12B show the confocal examination of flow chamber studies of strain NTHi 2019lsgG::gfp at day four (12A and 12B). FIG. 12B represents a vertical cross-section of the Z-series shown in FIG. 12A.

FIG. 15A is a view of the top surface of the bioflim. The surface has cracked during the desiccation and dehydration processes, but the matrix of the bioflim surrounding organisms can be seen. FIG. 15B shows a cross-sectional view of the bioflim. The coverslip surface upon which the biofilm formed is at the top. Multiple water channels can be seen throughout the biofilm. FIG. 15C shows a higher magnification of the cross-sectional view. Fibrillous material can be seen connecting the organisms within the biofilm. The scale bars are given on each image.

FIG. 20B shows the results of NeuAc incorporation after 24 hour growth of NTHi 2019 nanA (▦) and NTHi 2019 nanA::pgm (▩) in defined medium in the presence of $^{14}C$ NeuAc. Each result represents the results of studies from nine individual wells. The error bars represent 1 standard deviation. This study demonstrates that NTHi 2019 nanA::pgm is incorporating NeuAc into a carbohydrate structure. Since this mutant cannot incorporate NeuAc into its LOS, the NeuAc is most likely being incorporated into biofilm. The uptake in six control wells to which bacteria were not added is also shown (■).

DETAILED DESCRIPTION OF THE INVENTION

I. Definitions

Figure 1:
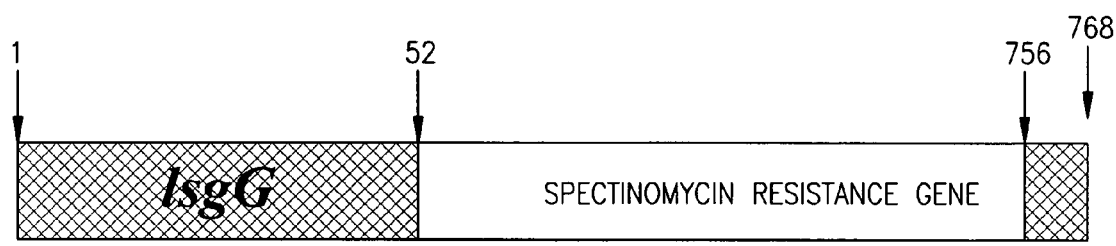
FIG. 1 depicts the LsgG deletion-replacement used to transform NTHi 2019 to generate a chromosomal lsgG deletion.

A "biofilm" is a complex organization of bacteria that are anchored to a surface via a bacterially extruded exopolysaccharide matrix, and grow into differentiated towers that can be several hundred bacteria in height (Costerton et al., 1999). The extruded exopolysaccharide matrix, which comprises more than 90% of the biofilm, envelopes the bacteria and provides protection from phagocytosis and oxidative burst mechanisms, both in natural environments and in the host. Bacteria within biofilms are also resistant to the host's humoral defense systems because or a lack of accessibility by immunoglobulin and complement. The attachment of bacteria to a surface triggers the expression of a cassette of genes, which results in the formation of a biofilm. A "biofilm phenotype" confers to a bacterium a reduced metabolic activity and enhanced antibiotic resistance in comparison with the corresponding planktonic phenotype. A "biofilm-producing bacterium" or "biofilm bacterium" is a bacterium capable of producing, forming, and/or accumulating a biofilm in vitro or in vivo, e.g., on artificial and mucosal surfaces. Biofilm-producing bacteria include, but are not limited to, *Haemophilus influenzae*. Biofilm bacteria have been demonstrated to be highly resistant to growth in standard planktonic culture, attributed to differences in gene expression.

As used herein, "disrupted gene" refers to an insertion, substitution, or deletion either in a gene of interest or in the vicinity of the gene, i.e., upstream (5') or downstream (3') of the gene, which results in the reduction of the biological activity or the loss of substantially all of the biological activity associated with the gene's product. For example, a disrupted gene involved in biofilm production and/or formation (a "biofilm-gene"), e.g., LsgG or Rfe, would be unable to express a protein related to the production or formation of a biofilm (a "biofilm protein" or a "biofilm peptide"), e.g., a protein associated with molybdate uptake and incorporation, fumerate metabolism, iron utilization, carbohydrate biosynthesis and cross-linking, and anaerobic respiration. A gene can be disrupted by any one of a number of methods known to the art.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucl. Acids Res.*, 19:508 (1991); Ohtsuka et al., *JBC*, 260:2605 (1985); Rossolini et al., *Mol. Cell. Probes*, 8:91 (1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid", "nucleic acid molecule", "nucleic acid fragment", "nucleic acid sequence or segment", or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The terms "protein," "peptide" and "polypeptide" are used interchangeably herein.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, N.Y.: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., *Mol. Biotech*., 3:225 (1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller, *CABIOS*, 4:11 (1988); the local homology algorithm of Smith et al., *Adv. Appl. Math.*, 2:482 (1981); the homology alignment algorithm of Needleman and Wunsch, *JMB*, 48:443 (1970); the search-for-similarity-method of Pearson and Lipman, *Proc. Natl. Acad. Sci. USA*, 85:2444 (1988); the algorithm of Karlin and Altschul, *Proc. Natl. Acad. Sci. USA*, 87:2264 (1990), modified as in Karlin and Altschul, *Proc. Natl. Acad. Sci. USA*, 90:5873 (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988); Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994). The ALIGN program is based on the algorithm of Myers and Miller, supra. The BLAST programs of Altschul et al., *JMB*, 215: 403 (1990); *Nucl. Acids Res.*, 25:3389 (1990), are based on the algorithm of Karlin and Altschul supra.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, *J. Mol. Biol.* 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, N.Y. (1993). Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, *Proc. Natl. Acad. Sci. USA*, 82:488 (1985); Kunkel et al., *Meth. Enzymol.*, 154:367 (1987); U.S. Pat. No. 4,873,192; Walker and Gaastra, *Techniques in Mol. Biol.* (MacMillan Publishing Co. (1983), and the references cited therein. Guidance as to appropriate amino acid substitutions that do not affect biological activity of the protein of interest may be found in the model of Dayhoff et al., *Atlas of Protein Sequence and Structure* (Natl. Biomed. Res. Found. 1978). Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, supra. See also Innis et al., *PCR Protocols*, Academic Press (1995); and Gelfand, *PCR Strategies*, Academic Press (1995); and Innis and Gelfand, *PCR Methods Manual*, Academic Press (1999). Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment", as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides. If not employed for expressing, a "portion" or "fragment" means at least 9, preferably 12, more preferably 15, even more preferably at least 20, consecutive nucleotides, e.g., probes and primers (oligonucleotides), corresponding to the nucleotide sequence of the nucleic acid molecules of the invention.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

II. Exemplary Biofilm-Genes

Attachment of planktonic ("free-floating") bacteria to a surface triggers the expression of a cassette of genes, which results in the "biofilm phenotype." These phenotypic changes, analogous to sporulation or starvation survival, occur via the induction of RNA polymerase-associated sigma factors or through sensor-regulator proteins that are activated on attachment. Accordingly, a biofilm-gene of the invention is any gene associated with the biofilm-phenotype. For example, in NTHi, biofilm genes include LsgG and Rfe.

LsgG is a global regulator that controls the expression of a number of bacterial processes in NTHi, including molybdenum uptake and incorporation, proteins involved in anaerobic respiration and a family of cross-linking enzymes involved in complex carbohydrate metabolism.

NTHi Rfe is a homolog of enzymes in other bacteria that are responsible for the addition of the first sugar to the carrier lipid upon which the carbohydrates are assembled. The gene product of Rfe is a homolog of undecaprenyl-phosphate alpha-N-acetylglucosaminyltransferase, which is involved in the addition of the first sugar to the carrier lipid upon which the biofilm is assembled in NTHi.

III. Expression of Biofilm Genes and Biofilm Peptides of the Invention

The biofilm genes and gene products of the invention may be produced in host cells, particularly in the cells of microbial hosts, using techniques known to the art. Host cells for expression of the instant genes and nucleic acid molecules are microbial hosts that can be found broadly within the fungal or bacterial families and that grow over a wide range of temperature, pH values, and solvent tolerances.

Because of transcription, translation and the protein biosynthetic apparatus is the same irrespective of the cellular feedstock, functional genes are expressed irrespective of carbon feedstock used to generate cellular biomass. Large scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strain s include but are not limited to fungal or yeast species such as *Aspergillus, Trichoderma, Saccharomyces, Pichia, Candida, Hansenula*, or bacterial species such as *Haemophilus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

Microbial expression systems and expression vectors containing regulatory sequences that direct high level expression of foreign proteins are well known to those skilled in the art. Any of these could be used to construct chimeric genes for production of the any of the biofilm gene products of the instant invention. These chimeric genes could then be introduced into appropriate microorganisms via transformation to provide expression.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the expression cassettes in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRPI, URA3, LEU2, ENO, TPI (useful for expression in *Saccharomyces*); AOX1 (useful for expression in *Pichia*); and lac, ara, tet, trp, (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

To confirm the presence of the biofilm gene or biofilm peptide in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of biofilm, e.g., O'Toole-Kolter test, or detecting the presence of endotoxin, e.g., using a Limulus amebocyte lysate assay; by microscopic methods, e.g., scanning electronic microscopy; immunological means, e.g., immunoprecipitations, immunoaffinity columns, ELISAs and Western blots; by continuous flow chamber analysis, or by any other assay useful to identify biofilm genes and/or peptides falling within the scope of the invention.

To detect and quantitate bacterial mRNA, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the presence of a biofilm gene DNA, they do not provide information as to whether the gene or DNA segment is being expressed. Expression may be evaluated by specifically identifying the peptide products of the DNA sequences or evaluating the phenotypic changes brought about by the expression of the introduced DNA segment in the host cell.

IV. Diseases and Conditions Amenable to the Methods of the Invention

Bacterial biofilms have been implicated in a number of conditions and diseases, for example, endocarditis, pneumonia in cystic fibrosis, prosthetic infections, dental caries and dental plaque, and associated periodontal disease. In addition, biofilm-like pseudomonal aggregates are found in the lungs of patients with cystic fibrosis (CF) (Singh et al., Nature, 407, 762-764 (2000)). Several lines of evidence suggest that NTHi grows as a biofilm in the human respiratory tract. The respiratory tract has been shown to harbor multiple strains of NTHi in several clinical settings, e.g., cystic fibrosis (CF), chronic bronchitis (CB), chronic obstructive pulmonary disease (COPD) and otitis media (OM). Any bacterial infection associated with the presence of a biofilm is amenable to treatment using the methods and/or vaccine of the invention. Therefore, it will be understood that the following list is exemplary rather than exhaustive.

Otitis Media

Otitis media (OM) is the most common reason for an ill child to visit a physician or other health care professional and is the most common reason for a child in the United States to receive antibiotics or undergo a general anesthetic. The underlying pathophysiology of OM is poorly understood although it is clear that OM results from an interplay of infectious, environmental, and host genetics factors.

NTHi is the causative agent of acute OM as established by pure culture of the organism from middle ear fluid during disease. In addition, nontypeable *H. Influenzae* has been implicated as a cause of otitis media with effusion, which refers to the presence of fluid in the middle ear in the absence of acute symptoms. Although most effusions from acute OM are culture-positive for bacteria (predominantly *Haemophilus influenzae, Streptococcus pneumonia*, and *Moraxella catarrhalis*), the majority of chronic effusions are cultural-negative, refractory to antibiotic treatment, and positive for a variety of inflammatory mediators.

Chronic Bronchitis

NTHi has been recovered from the lower airways of stable and of acutely ill chronic bronchitis (CB) patients, whereas it was not found in the lower respiratory tract of healthy adults. In patients with CB, NTHi appears to be associated with recurrent and/or persistent infections of the lower respiratory tract. NTHi appears to be able to persist in the lower respiratory tract for months and can be isolated even after or during antimicrobial treatment (Bandi et al., *Am. J. Respir. Crit. Care Med.*, 164, 2114-2119 (2001).

V. Vaccines of the Invention

The present invention provides a vaccine for use to protect mammals against the colonization and/or infection associated with the presence of biofilm-bacteria, e.g., otitis media, chronic bronchitis and the like. In one embodiment of this invention, as is customary for vaccines, a biofilm peptide, e.g., lsgG, rfe, variants or fragments thereof, can be delivered to a mammal in a pharmacologically acceptable vehicle. As one skilled in the art will appreciate, it is not necessary to use the entire gene product (i.e., peptide or protein). A selected portion of the polypeptide (for example, a synthetic immunogenic polypeptide corresponding to a portion of the lsgG) can be used.

As one skilled in the art will also appreciate, it is not necessary to use a polypeptide that is identical to a native biofilm peptide's amino acid sequence. The amino acid sequence of the immunogenic polypeptide can correspond essentially to the corresponding native protein's amino acid sequence. As used herein "correspond essentially to" refers to a polypeptide sequence that will elicit a protective immunological response at least substantially equivalent to the response generated by a native biofilm peptide. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response.

Alternatively, the biofilm peptide can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin. Useful immunogenic polysaccharides include group A *Streptococci* polysaccharide, C-polysaccharide from group B *Streptococci*, or the capsular polysaccharide of *Streptococci pnuemoniae*. Alternatively, polysaccharides of other pathogens that are used as vaccines can be conjugated or linked to the biofilm peptide.

To immunize a subject, the biofilm peptide, or an immunologically active fragment, variant or mutant thereof, is administered parenterally, usually by intramuscular or subcutaneous injection in an appropriate vehicle. Other modes of administration, however, such as oral delivery or intranasal delivery, are also acceptable. Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required to maintain a state of immunity to the biofilm-producing bacterium of interest, e.g., *Haemophilus influenzae*.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified biofilm peptide, fragment, variant, or mutant thereof, can be isolated, lyophilized and stabilized. The biofilm peptide may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.*, 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

The application of a biofilm peptide, subunit or mutant thereof, for vaccination of a mammal against colonization of a biofilm producing bacterium offers advantages over other vaccine candidates.

VI. Formulations of Vaccines and Methods of Administration

The vaccines of the invention may be formulated as pharmaceutical compositions and administered to a mammalian host, such as a human patient, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s). The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following examples are intended to illustrate but not limit the invention.

EXAMPLE 1

In order to study the effect of lsgG on biofilm formation, a mutation was made in the lsgG (HI1693) by the deletion of 704 nucleotides of this gene from base 52 to 756. A spectinomycin resistance gene was ligated into the site of this deletion and the resulting construct was transformed by homologous recombination into the chromosome of NTHi strain 2019 (FIG. 1). Strains containing the mutated lsgG locus were selected on spectinomycin BHI plates. The site of mutant insertion into the lsgG gene was confirmed by PCR of chromosomal DNA and Southern blots. The amino acid and nucleotide for LsgG sequence is shown in FIG. 2.

EXAMPLE 2

Figure 3:
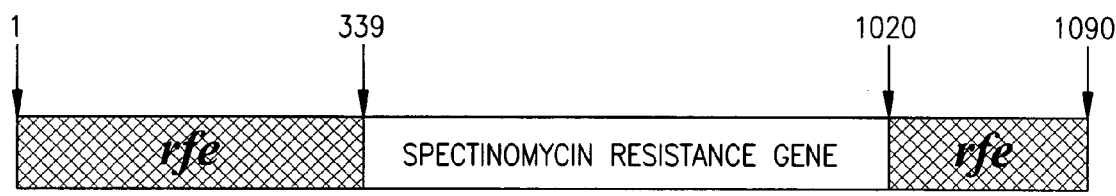
FIG. 3 depicts the rfe deletion-replacement used to transform NTHi 2019 to generate a chromosomal rfe deletion.

NTHi Rfe is a homolog of enzymes in other bacteria, which are responsible for the addition of the first sugar to the carrier lipid upon which the carbohydrates are assembled. A mutation was made in NTHi 2019 rfe by the deletion of 681 nucleotides from base 339 to 1020 and replace with a spectinomycin resistance cassette (FIG. 3). The amino acid and nucleotide sequence for Rfe is shown in FIG. 4.

EXAMPLE 3

To confirm that lsgG is a global regulatory gene, we performed gene chip array analysis comparing the RNA obtain from the NTHi 2019 lsgG spectinomycin mutant with RNA obtained from strain NTHi 2019 grown in BHI broth cultures for six hours. The results of these studies demonstrated that the expression of 59 genes was increased over 2 fold in the wildtype NTHi 2019 when compared to the mutant (Table 1). Genes whose expression was regulated included genes involved in molybdate uptake and incorporation, genes involved in fumerate metabolism, iron utilization, carbohydrate biosynthesis and cross-linking and a number of genes involved in anaerobic respiration. This chip array data strongly suggested that lsgG may play a role in biofilm formation since both carbohydrate cross-linking genes and genes involved in anaerobic respiration were regulated. Both are important factors in biofilm formation and the ability of the bacteria to survive within the reduced oxygen environment of a biofilm.

EXAMPLE 4

Figure 5:
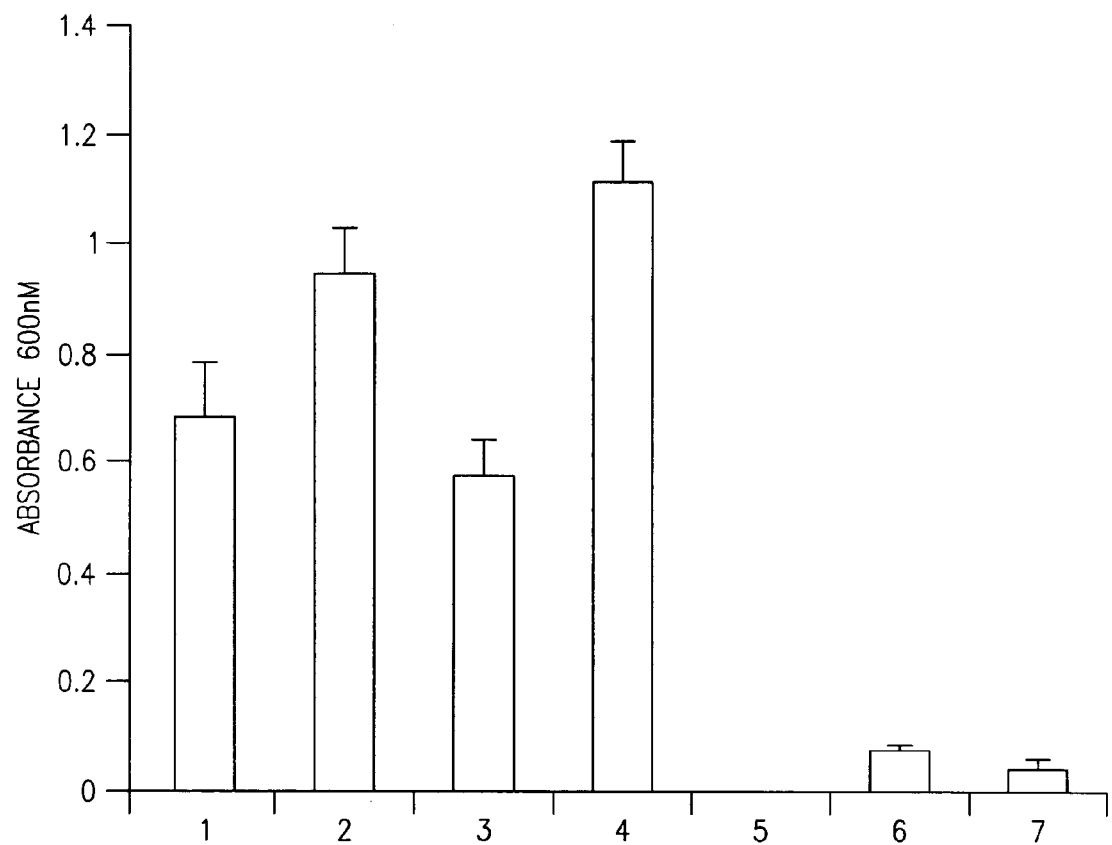
FIG. 5. O'Toole-Kolter assay showing evidence of biofilm formation by NTHi and the effects on biofilm formation by lsgA, rfe and lsgG mutations. Lane 1, 2, and 3 are NTHi strain 2019, 3198, 7502, lane 4 contains NTHi2019 lsgA, lane 6 contains NTHi 2019 lsgG and lane 7 contains NTHI 2019rfe. The results are presented as the mean of four independent experiments and the error bars equal one standard deviation. The values obtain with the lsgG and rfe were statistically highly significant ($p<0.005$) when compared to biofilm produced by NTHi 2019 using paired T-test analysis.

A test for biofilm formation is the O'Toole—Kolter test. In this test, bacteria are grown in BHI in wells in a 96 well microtiter dish overnight. Twenty microliters of 1% crystal violet is added to each well. This solution is removed and the plate is washed with PBS. Two hundred microliters of methanol are added to the well. If a biofilm is present, crystal violet is retained after staining. With the addition of the methanol, the crystal violet dissolves in the methanol and the resulting intensity of the blue color can be read in a microtiter plate reader at an OD of 600 nm. FIG. 5 shows the results obtained with nontypeable *H. influenzae* strain 2019 and the 2019 mutants in the genes described. These studies show that three wildtype NTHi strains 2019, 7502 and 3198 and NTHi 2019lsgA produced biofilms. Studies with the strain 2019lsgG, and 2019rfe are also shown. Biofilm production is shown to be reduced at least nine fold in the 2019 lsgG mutant. NTHi 2019 rfe is involved in the first step in complex bacterial carbohydrate synthesis by placing a sugar (usually a hexosamine) onto a carrier lipid. These studies demonstrated that no biofilm was made when NTHi 209rfe was mutated.

EXAMPLE 5

Figure 6A:
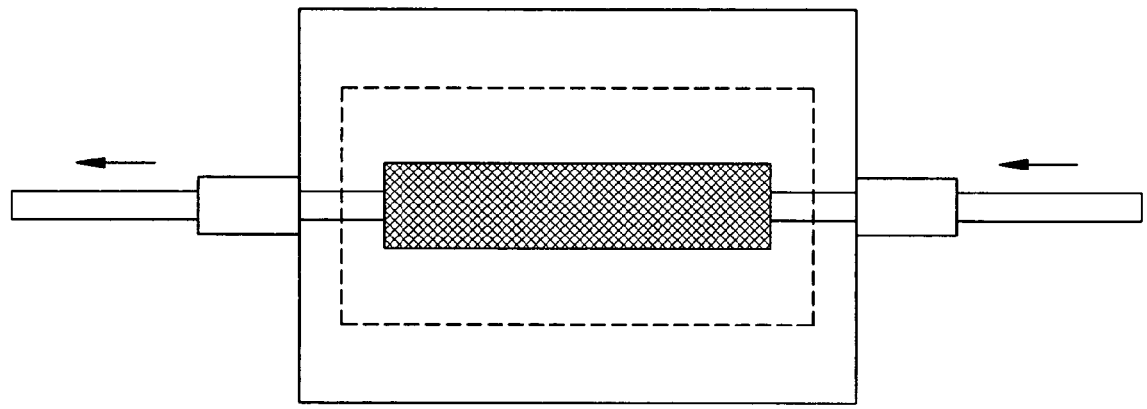
FIGS. 6A and 6B. Continuous flow chamber for the analysis of bioflim formation by NTHi.
Figure 6B:
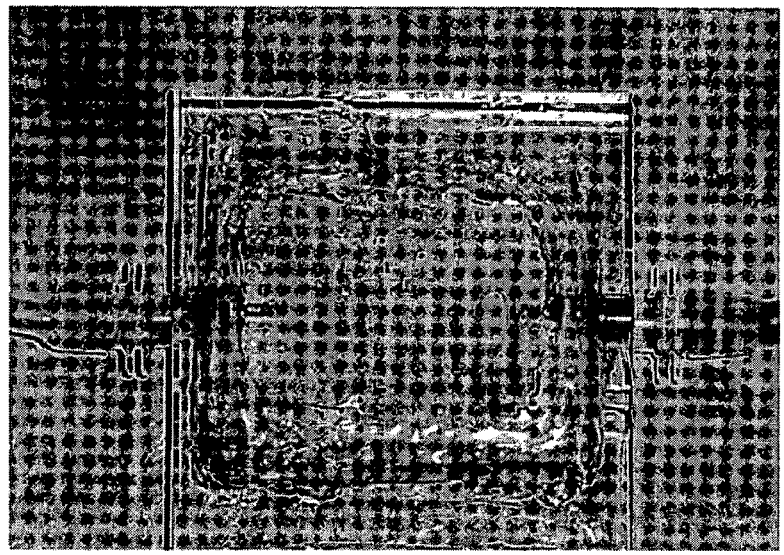

In order to evaluate biofilm formation on a glass surface with NTHi 2019, NTHi 2019lsgG and NTHi 2109rfe, studies were performed in a continuous flow chamber with these organisms (FIG. 6) over a six-day experimental period. All of the strains utilized in these experiments express the green fluorescent protein that was carried on the low copy number plasmid, pACYC184. The chambers were examines using a laser scanning confocal microscope every 24 hours over the six-day period. Evidence of biofilm formation could be found with the wildtype NTHi strain 2019 but not with either NTHi 2019lsgG or NTHi 2019rfe (FIG. 7).

EXAMPLE 6

In order to evaluate the ability of NTHi and the lsgG and rfe mutants to produce biofilms on a human epithelial surface, four-day NTHi infections were performed on primary human bronchial epithelial cells grown in tissue culture. The results of these studies are shown in FIG. 8. As can be seen an extensive microbial biofilm extends over the primary bronchial epithelial surface by day four in the cells infected with NTHI strain 2019. Studies of the NTHi 2019lsgG and NTHi 2019rfe mutants showed no biofilm formation by day four (FIG. 7).

EXAMPLE 7

The abbreviations used in this example are: NTHi, nontypeable *Haemophilus influenzae*; CFU, colony forming units; LOS, lipooligosaccharide; SEM, scanning electron microscope; Kdo, 2-keto-3-deoxy-D-manno-octulosonic acid; PEA, phosphoethanolamine; NeuAc, N-acetylneuraminic acid; CMP-NeuAc, cytidine monophosphate N-acetylneuraminic acid; PBS; phosphate buffered saline; LPS, lipopolysaccharide; PCR, polymerase chain reaction; gfp, green fluorescent protein; kb, kilobase pair: EDTA, ethylenediaminetetraacetic acid; PBS, phosphate-buffered saline; ELISA, enzyme-linked immunosorbent assay; LOS, lipooligosaccharide; MALDI-MS, matrix assisted laser desorption ionization mass spectrometry; ChoP, phosphorylcholine; GalNAc, N-acetylgalactosamine; Hex, hexose; HexNAc, N-acetylhexosamine; Hep, L-glycero-D-mannoheptose or D-glycero-D-manno-heptose; P, phosphate; TOF, time-of-flight mass analyzer; $[M-H]^-$, deprotonated molecular ion; m/z, mass to charge ratio; FITC, fluorscein isothiocyanate; TRITC, texas red isothiocyanate; OCT, optimal cutting temperature.

Previous studies have suggested that nontypeable *Haemophilus influenzae* (NTHi) strains can form biofilms during human and chinchilla middle ear infections. Microscopic analysis of a five-day biofilm from NTHi 2019 grown in a continuous flow chamber demonstrated a biofilm with a diffuse matrix interlaced with multiple water channels. Studies disclosed herein show that biofilm production is significantly decreased in a chemically-defined medium lacking N-acetylneuraminic acid (sialic acid). Based on these observations, NTHi 2019 mutations were examined in seven genes involved in carbohydrate and lipooligosaccharide biosynthesis. NTHi 2019 mutants in CMP-NeuAc synthetase (siaB), one of the three NTHi sialyltransferases (siaA), and a homolog of undecaprenyl-phosphate α-N-acetyl-glucosaminyl-transferase (wecA) produced significantly reduced amounts of biofilm. NTHi 2019 mutations in phosphoglucomutase (pgm), UDP-galactose-4-epimerase, and two other NTHi sialyltransferases (lic3A and lsgB) produced biofilms equivalent to or greater than the parent strain. The NTHi 2019 pgm biofilm was studied with the *Maachia amurensis*-FITC and *Sambucus nigra*-TRITC lectins. *Sambucus nigra*-TRITC lectin bound to this biofilm while *Maachia amurensis*-FITC lectin did not. *Sambucus nigra*-TRITC lectin binding was reversed by inhibition with αα→6 neuraminyllactose and by treatment of the biofilm with *Vibrio cholera* neuraminidase prior to incubation with this lectin. MALDI-TOF analysis of lipooligosaccharide isolated from the biofilm, planktonic phase, and plate-grown organisms showed most sialylated glycoforms increase 2-fold to 4-fold when the LOS is derived from planktonic or biofilm organisms. These studies indicate that NTHi 2019 produces a biofilm containing αα→6 linked sialic acid and that the sialic acid content of lipooligosaccharides increases concomitantly with the organisms transition to a biofilm form.

Introduction

Bacterial biofilms have been defined as communities of bacteria intimately associated with each other and included within an exopolymer matrix. These biological units exhibit their own properties, which are quite different in comparison with those showed by the single species in planktonic form (1). Numerous bacterial species are capable of producing biofilms.

Nontypeable *Haemophilus influenzae* (NTHi) is a gram-negative cocco-bacillus that frequently colonizes the human nasopharynx. NTHi is a frequent cause of otitis media in children (2) and acute bronchitis and pneumonia in patients with chronic obstructive pulmonary disease (3). Studies in a chinchilla otitis media model infected with NTHi have indicated that biofilms are produced as a part of this infection (4). Ehrlich et al. have shown scanning electron microscopy (SEM) and confocal images of biofilm formation on tympanostomy tubes collected from children with otitis media (4).

The purpose of this study was to identify NTHi genes involved in biofilm biosynthesis. Using several different techniques to identify biofilm formation, mutations in NTHi genes homologous to a undecaprenyl-phosphate α-N-acetyl-glucosaminyl-transferase (wecA) were shown to produce little to no biofilm. In addition, a mutant in a NTHi sialyl-transferase (siaA) and a mutant in CMP-NeuAc synthetase (siaB) resulted in significantly reduced biofilm production. Lectin studies and enzymatic analysis suggested that the sialic acid (N-5-acetylneuraminic acid, NeuAc) was a terminal sugar attached to a N-acetyl-hexosamine (probably N-acetyl-galactosamine) in an αα-6 linkage. A number of sialylated lipooligosaccharide (LOS) glycoforms increased during the biofilm and planktonic growth.

Experimental Procedures

Bacteria and culture conditions: The bacterial strains used in this study are described in Table 1.

TABLE 1

Bacterial Strains and Vectors

| Strain or Plasmid | Genotype | Source or Reference |
| --- | --- | --- |
| pGBgfp::cat | gfp in pGB2 | Herein (6) |
| NTHi 2019 | non-typeable *Haemophilus influenzae* | Ref. (9) |
| NTHi 2019:gfp | gfp-expressing NTHi 2019 | Herein |
| NTHi 2019 galE | UDP-galactose-4-epimerase | Herein (51) |
| NTHi 2019 lic3A | sialyltransferase | (47,52) |
| NTHi 2019 lsgB | sialyltransferase | (47) |
| NTHi 2019 pgm | phosphoglucomutase | (53) |
| NTHi 2019 pgm::gfp | gfp-expressing HTHI 2019pgm | Herein |
| NTHi 2019 wecA | undecaprenyl-phosphate α-N-acetylglucosaminyltransferase | Herein |
| NTHi 2019 wecA::gfp | gfp-expresing NTHi 2019wecA | Herein |
| NTHi 2019 siaA | sialyltransferase | (47) |
| NTHi 2019 siaB | CMP-NeuAc synthetase | (29) |
| NTHi 2019 siaB::gfp | gfp-expressing NTHi 2019siaB | Herein |
| NTHi 2019 nanA | N-acetylneuraminate lysase | |
| NTHi 2019 nanA::pgm | N-acetylneuraminate lysase, Phosphosglucomutase | This study |

NTHi strain 2019 is a clinical isolate from a patient with chronic obstructive pulmonary disease (5). This strain was reconstituted from a frozen stock culture and propagated on brain heart infusion (BHI) agar (Difco, Detroit, Mich.) supplemented with 10 μg/ml hemin (Sigma Chemical Co., St. Louis, Mo.) and 10 μg/ml nicotinamide adenine dinucleotide (NAD, Sigma) at 37° C., 5% $CO_2$.

Construction of gfp expressing NTHi: NTHi strains were transformed with the plasmid pGB2:cat (6) expressing green fluorescent protein (gfp) using a modification of the method of Williams et al. (7).

Construction of NTHi 2019galE: Previous studies have shown that galactose-4-epimerase is encoded by gene HI0351 in the Institute for Genomics database (8). Using the upstream primer 5'GCTGGTTATATCGGTTCT3' (SEQ ID NO:5) and the downstream primer 5' GATCAGAATAG-CAAGTCGC3' (SEQ ID NO:6), a 882 bp fragment of DNA was amplified from NTHi 2019 chromsomal DNA and ligated into pCR2.1. This fragment was sequenced and shown to contain almost the entire HI0351 (galE). A unique Eco47RIII site at bp 737 was identified in galE. The gene was digested, and an erythromycin-resistance cassette was cloned into this site. The mutation was confirmed by restriction digestions. The plasmid containing the mutated galE gene was linearized and transformed into NTHi 2019 as previously described (9). The mutation was confirmed by PCR and Southern Blot analyses of the chromosomal NTHi 2019 galE DNA.

Construction of wecA::spec deletion mutant: To construct a deletion mutation in NTHi 2019 wecA (HI1716), a NTHi 2019 phagmid genomic library was screened with a wecA digitoninin-labeled probe. Positive plaques were purifed, and excision was performed. The plasmid pBK-CMVHIA2wecA was isolated, and sequencing verified the presence of HI1714, HI1715, wecA (HI1716), and 912 bp of the 3' end of HI1719 in a 3449 bp insert. The gene order in strain 2019 is different than *H. influenzae* RDKW20, and open reading frames HI1718 and HI1719 are not adjacent to HI1716. This fragment was moved into pGEM3Zf(+) at the SacI and SamI sites. The plasmid was restricted with BclI and NsiI. This removed 682 bp of sequence internal to wecA. A spectinomycin-resistance (spec) cassette was cloned into the BclI and NsiI sites. This construct was verified by DNA sequencing and diagnostic DNA restriction enzyme digests. The mutation was introduced into NTHi 2019 by linearizing the plasmid construct as above. Transformants were plated onto supplemented BHI agar containing 25 μl of spectinomycin. Confirmation of the deletion mutation in NTHi 2019 wecA was determined by PCR and Southern Blot analyses.

Construction of nanA::kan deletion mutant: In order to study the incorporation of NeuAc into biofilm, mutations were made in the *Haemophilus* N-acetylneuraminate lysase gene, nanA (TIGR locus HI0142). The DNA sequence from *H. influenzae* Rd KW-20 was used to construct two primers 5'-CCTACGATATGAATAGGATCATTACG-3' (SEQ ID NO:7) and 5'-CAGTAGCTAACCCCAATACAAAAG-3' (SEQ ID. NO:8). The polymerase chain reaction was used to amplify a 2612 bp fragment of DNA which was cloned into pCR2.1-TOPO (InVitrogen, Carlsbad, Calif.). The fragment was removed by EcoRI digestion, inserted into an EcoRI digested pUC19, verifed to contain *Haemophilus* nanA by sequencing, and a kanamycin cassette was inserted into nanA using TN::EX<KAN2> (Epicentre, Madison, Wis.) according to manufacturer's instructions. The plasmid containing the mutated nanA gene was linearized and transformed into NTHi 2019 and NTHi 2019 pgm as previously described (9). The presence of the kan cassette within nanA in both mutants was confirmed by PCR and Southern blot analyses.

Biofilm growth assay: Biofilm produced by NTHi 2019 and the NTHi 2019 mutants described in Table 1 was analyzed using the microtiter plate assay described by O'Toole-Kolter (10,11). This assay is referred herein as the O'Toole-Kolter assay. An overnight broth culture of each strain in BHI was diluted 1:200 in fresh broth. 200 μl of these suspensions were inoculated in quadruplicate into outside wells of a 96 well tissue culture plate (Nalgene Nunc International Co., Naperville, Ill.). The plates were incubated at 37° C., 5% $CO_2$ for 24 hours. Before biofilm quantitation, growth was assessed by measuring the $OD_{490}$. To quantitate biofilm formation, 20 µl of crystal violet (Fisher Scientific, Pittsburgh, Pa.) was added to each well, and plates were incubated at room temperature for 15 minutes. Plates were then washed vigorously with distilled water and air-dried. A volume of 230 µl of 95% ethanol was added to each well, and the $OD_{600}$ was measured. All strains were tested in quadruplicate and average biofilm formation was calculated from three different experiments.

$^{14}$C NeuAc incorporation studies: Studies were performed to compare $^{14}$C NeuAc incorporation into NTHi 2019 nanA and NTHi 2019 nanA::pgm biofilms. The strains were grown for 24 hours in microtiter wells at 37° C. in 5% $CO_2$ in RPMI (Gibco, Grand Island, N.Y.) supplemented with 0.5 µg/ml protoporphyrin IX, 10 µg/ml NAD, 20 µM NeuAc and 82.5 nCi/ml $^{14}$C NeuAc (55 mCi/mM, American Radiolabeled Chemicals, Inc., St. Lousi, Mo.). The medium was carefully removed from each well and the wells washed three times with distilled water. The biofilm was harvested in 100 µl of Microscint© (Packard Meridian, Conn.) and 30 µl from each well was counted in a TopCounter™ (Parchard, Downers Grove, Ill.).

Laser scanning confocal microscopy (LSCM) in a continuous flow chamber: To access biofilm formation, gfp-expressing NTHi were grown in a flow chamber the size of which was 5×35×1 mm, similar to those described previously (12). The biofilm medium was composed of Morses Defined Medium (13) diluted 1:10 with PBS and supplemented with 10 µg/ml hemin, 10 µg/ml NAD, and 1 µg/ml chloramphenicol (Sigma). Depending on the experimental conditions, 20 µM NeuAc (Sigma) was added to this medium. To infect the flow chamber, approximately $10^8$ CFU/ml in fresh biofilm medium was placed in the chamber at 37° C. for one hour. Biofilm medium flow was then started and maintained at a constant rate of 180 µl/min. For NeuAc-free experiments, protoporphyrin IX (0.5 µgm/ml) was added to the medium in place of hemin. Confocal images were obtained using a Bio-Rad scanning confocal microscope. All the microscopes used in these studies are located at the Central Microscopy Research Facility at the University of Iowa (Iowa City, Iowa).

Live/Dead staining of biofilm from continuous flow chamber: For evaluation of the live and the dead bacteria present in the biofilm matrix, NTHi 2019 was grown in a flow chamber as described above. After 2 or 5 days, the flow chamber was carefully disconnected. The LIVE/DEAD BacLight bacteria viability kit (Molecular Probes, Eugene, Oreg.) was used to visualize the live and the dead bacteria within the biofilm. Briefly, SYTO 9 (Component A) and propidium iodide (Component B) were mixed in a 1:1 ratio. Three microliters of the viability stain were added to 1 ml of PBS. Medium in the chamber was aseptically replaced with the stain-PBS mixture. The chamber was incubated for 15 minutes at 37° C. One ml of sterile PBS was then added to the chamber to flush away excess stain. The chamber was immediately visualized using the Zeiss Confocal microscope at 10× magnification. The images were compiled as cross-sections of a z-series.

SEM analysis of the biofilm: Biofilms were processed for scanning electron microscopy (SEM) and viewed using the Hitachi S-4000 scanning electron microscope (14). Briefly, coverslips were fixed in a 2% osmium tetroxide/perfluorocarbon solution for 2 hours, dehydrated with three 100% ethanol washes, and dried using a critical point dryer to preserve biofilm formation. The coverslips were then mounted onto stubs using colloidal silver and sputter-coated with gold palladium.

Lipooligosaccharide preparation and neuraminidase treatment: LOS was prepared by a modification of the Hitchcock and Brown method (15). Organisms were grown on a solid BHI medium supplemented with 10 µg/ml hemin, 10 µg/ml NAD, and 20 µM NeuAc. Organisms from a single plate were suspended in 2 ml of PBS to a final $OD_{650}$ of 0.9. Bacteria were washed twice with PBS, resuspended in 200 µl of lysis buffer (0.06 M Tris, 10 mM EDTA, 2.0% SDS, pH 6.8) and incubated in a boiling water bath for 5-10 minutes. The samples were allowed to cool, and 30 µl of a proteinase K (Sigma) solution (2.5 mg/ml diluted in lysis buffer) was added to 150 µl of the boiled sample. The samples were incubated at 37° C. for 16-24 hours. LOS was precipitated by adding 1/10 volume of 3 M sodium acetate and 2 volumes of 100% ethanol, put on dry ice for 10 minutes or in a −80° C. freezer for 1 hour, and then centrifuged at 15,000×g for 5 minutes. The samples were washed twice with 70% ethanol and brought up in dd$H_2$O to a final volume of 180 µl and lyophilized.

O-deacylation of LOS samples: LOS (<100 µg) from planktonic and biofilm H. influenzae strain 2019 was O-deacylated by treatment with 30 µl of anhydrous hydrazine (Sigma) at 37° C. for 40 minutes, with occasional vortexing. Samples were then cooled in an ice bath, treated with 5 volumes of ice-cold acetone added drop-wise, and allowed to sit at −20° C. for 1 hour. After centrifugation (12,000×g, 30 minutes, 4° C.), the supernatants were removed and the pelleted O-deacylated LOS was washed with 100 µl of chilled acetone and centrifuged a second time (12,000×g, 30 minutes, 4° C.). Following removal of the supernatants, the pellets were dissolved in 100 µl of Milli-Q de-ionized water (Millipore, Corp., Billerica, Mass.) and centrifuged a third time (12,000×g, 30 minutes, 4° C.) to remove traces of water-insoluble material remaining in the samples. Finally, the supernatants (water-soluble O-deacylated LOS) from this extra centrifugation were removed, transferred to new vessels, and evaporated to dryness. The LOS from plate-grown NTHi strain 2019 (0.5 mg) was O-deacylated in a similar fashion using 100 µl of anhydrous hydrazine.

Neuraminidase-treatment of O-deacylated LOS: To remove NeuAc, aliquots of the O-deacylated LOS samples (estimate <30 µg) were digested with immobilized neuraminidase from Clostridium perfringens type VI-A (Sigma) in 40 µl of 10 mM ammonium acetate, pH 6.0, for 21 hours at 37° C. The immobilized enzyme was pelleted by centrifugation (12,000×g, 20 minutes, 4° C.) and the supernatants were removed. Pellets were washed twice with 50 µl of buffer followed by centrifugation (12,000×g, 20 minutes, 4° C.). Combined supernatants were evaporated to dryness, redissolved in 50 µl of de-ionized water, and evaporated to dryness again.

Matrix-assisted laser desorption ionization-time of flight (MALDI-TOF) mass spectrometry: The O-deacylated LOS samples were analyzed by MALDI-TOF on a Voyager-DE mass spectrometer (Applied Biosystems, Foster City, Calif.) equipped with a nitrogen laser (337 nM). All spectra were recorded in the negative-ion mode using delayed extraction conditions as described in detail elsewhere (16). O-deacylated LOS was dissolved in 30 µl of de-ionized water, and 5 µl aliquots were desalted by drop dialysis on VSWP 0.025 µm pore size nitrocellulose membranes (Millipore Corp.) over de-ionized water for 80 minutes. Recovered drops were evaporated to dryness and then redissolved in 5 µl of de-ionized water. One µl aliquots of desalted O-deacylated LOS samples were then delivered into 0.5 ml microcentrifuge tubes containing a small amount of cation exchange resin (Dowex 50W-X8, $NH_4^+$ form, Bio-Rad, Hercules, Calif.). Subsequently, 1 µl aliquots of matrix solution (a saturated solution of 2,5-dihydroxybenzoic acid in acetone) were added to the samples. After brief mixing, 1 µl portions of the mixture were delivered to a stainless steel MALDI target and allowed to air dry. Approximately 200 laser shots were acquired for each sample. The spectra were smoothed with a 19-point Savitsky-Golay function and mass calibrated with an external mass calibrant consisting of renin substrate tetradecapeptide, insulin chain B (oxidized), and bovine insulin (all from Sigma). For comparison purposes, a two-point correction was then done on the spectra using the expected fragment ion for O-deacylated diphosophoryl lipid A (m/z 952.0) and the "$B_3$" glycoform of NTHi strain 2019 (m/z 2522.1). All masses are given as their average mass values.

Lectin Analysis of Biofilms: Five-day biofilms produced by strain NTHi 2019 pgm were subjected to lectin analysis. This strain was chosen because it can not produce an acceptor for NeuAC on its LOS, and our studies had shown that it was capable of forming a biofilm in amounts equal to or greater than the parent strain. The biofilm was fixed in 4% paraformaldehyde and embedded in situ in OCT resin (Sakura Finetek USA, Inc., Torrance, Calif.) on the cover slip surface upon which it was formed. After hardening, the cover slip was removed by freezing the sample in liquid nitrogen and shattering the glass, leaving the biofilm within the OCT resin. The biofilm was then cut into 1 µm thick sections. These section were studied using fluorescent microscopy with the following lectins; *Maachia amurensis*-FITC and *Sambucus nigra*-TRITC lectins (EY Laboratories, San Mateo, Calif.), Binding inhibition experiments were performed by pre-incubation of *Sambucus nigra*-TRITC for 30 minutes with N-neuramyllactose at a concentration of 200 µg/ml.

Statistical Analysis: Statistical Analyses using paired Student's T-test were performed using Statview for Macintosh.

Results

NTHI biofilm formation: Previous studies in the chinchilla middle ear infection model and microtiter plate biofilm assay have suggested that NTHi can form biofilms (4). Studies with NTHi strain 2019 in the O'Toole-Kolter microtiter plate assay suggested that this strain was capable of forming a biofilm. The ability of strain 2019 to form a biofilm was confirmed in a continuous flow chamber over 5 days of growth (FIG. 9A). A toluidine-blue stained frozen section of the NTHi 2019 biofilm embedded in OCT can be seen in FIG. 9B. This shows tightly packed matrix and organisms at the bottom of the biofilm with a more diffuse structure interlaced with water channels further from the slide surface. Higher magnification studies using SEM are seen in FIG. 10A-10C. At the top of this structure, a pellicle formed by the biofilm matrix can be seen (FIGS. 10A and 10B). FIG. 10C shows a lateral view of the channels at a higher magnification. Fibrils can be seen extending between the bacteria, which may be remnants of the biofilm matrix. Using a Live/Dead stain, it was demonstrated that at day 2, viable organisms predominated throughout the biofilm with dead organisms primarily localized to the glass slide surface on which the biofilm formed (FIG. 11A). In contrast, by day 5, the proportion of live organisms appeared to decrease and dead organisms were seen throughout the biofilm (FIG. 11B). This suggests that, in the continuous flow system, the NTHi biofilm may have a finite life span.

Analysis of LOS glycoforms: Gene expression changes in bacteria within biofilms (17). To more precisely examine the expression of LOS glycoforms in *H. influenzae* strain 2019 during growth as a biofilm, LOS was isolated from biofilm, planktonic, and plate-grown bacteria. Isolated LOS was O-deacylated by treatment with anhydrous hydrazine and analyzed by MALDI-TOF mass spectrometry. *H. influenzae* strain 2019 produces a complex mixture of LOS glycoforms when grown in culture medium (18,19). The major component of strain 2019 LOS contains a lactose moiety (Galβ1→4Glcβ1→) linked to $Hep^I$ of the common core structure ($Hep^{III}\alpha 1,2 \rightarrow Hep^{II}\alpha 1,3 \rightarrow Hep^{I}\alpha 1,5 \rightarrow$Kdo(P)→lipid A) characteristic of *H. influenzae* LOS (18,20,21). When strain 2019 was grown on solid medium supplemented with NeuAc for the present study, its LOS repertoire expanded to include new sialylated, disialylated, and polysialylated species (FIG. 12A and Table 2).

TABLE 2

List of LOS glycoforms observed in plate-grown, planktonic, and biofilm *H. influenzae* strain 2019.

| Glycoform | Proposed compositions | | | | | | Calculated [M − H]⁻ with: | | |
|---|---|---|---|---|---|---|---|---|---|
| | NeuAc | HexNAc | Hex | Hep | Kdo(P) | ChoP | 1PEA | 2PEA | 3PEA |
| Asialoglycoforms | | | | | | | | | |
| A | | | 1 | 3 | 1 | | 2113.8 | 2236.9 | 2360.0 |
| B | | | 2 | 3 | 1 | | 2276.0 | 2399.0 | 2522.1 |
| B¶ | | | 2 | 3 | 1 | 1 | 2441.1 | 2564.2 | 2687.2 |
| C | | | 3 | 3 | 1 | | 2438.1 | 2561.2 | 2684.2 |
| D | | | 4 | 3 | 1 | | 2600.3 | 2723.3 | 2846.4 |
| E | | | 5 | 3 | 1 | | 2762.4 | 2885.5 | 3008.5 |
| F | | 1 | 3 | 3 | 1 | | 2641.3 | 2764.4 | |
| G | | 1 | 4 | 3 | 1 | | 2803.5 | 2926.5 | |
| H | | 1 | 5 | 3 | 1 | | 2965.6 | 3088.7 | |
| Sialylated glycoforms | | | | | | | | | |
| B* | 1 | | 2 | 3 | 1 | | | 2690.3 | 2813.4 |
| B** | 2 | | 2 | 3 | 1 | | 2858.5 | 2981.6 | 3104.6 |
| D* | 1 | | 4 | 3 | 1 | | 2891.5 | 3014.6 | |
| D** | 2 | | 4 | 3 | 1 | | 3182.8 | 3305.8 | |
| E* | 1 | | 5 | 3 | 1 | | 3053.7 | 3176.7 | 3299.8 |
| E** | 2 | | 5 | 3 | 1 | | 3344.9 | 3468.0 | 3591.0 |

TABLE 2-continued

List of LOS glycoforms observed in plate-grown, planktonic, and biofilm *H. influenzae* strain 2019.

| Glycoform | Proposed compositions | | | | | | Calculated [M − H]⁻ with: | | |
|---|---|---|---|---|---|---|---|---|---|
|  | NeuAc | HexNAc | Hex | Hep | Kdo(P) | ChoP | 1PEA | 2PEA | 3PEA |
| F* | 1 | 1 | 3 | 3 | 1 |  |  | 3055.6 | 3178.7 |
| H* | 1 | 1 | 5 | 3 | 1 |  | 3256.9 | 3379.9 | 3503.0 |
| I* | 1 | 1 | 6 | 3 | 1 |  |  | 3542.1 | 3665.1 |
| I** | 2 | 1 | 6 | 3 | 1 |  | 3710.3 | 3833.3 | 3956.4 |
| I*** | 3 | 1 | 6 | 3 | 1 |  | 4001.5 | 4124.6 |  |

All components contain the O-deacylated lipid A moiety. Asterisks denote the number of NeuAc residues and the "¶" symbol represents a phosphorylcholine (ChoP) moiety. All masses listed are average values.

The sialylated and disialylated forms of the major Hex2 glycoform, $B_3^*$ and $B_3^{**}$, contain the sialyllactose moiety observed in other strains of *H. influenzae* (22-26). Asialo- and sialylated glycoforms containing HexNAc (whose proposed compositions are consistent with structures seen in other strains of *H. influenzae*) (27,28) were also more abundant in plate-grown strain 2019. Additionally, many of the higher molecular weight sialylated glycoforms observed are consistent with species seen in plate-grown *H. influenzae* type b strain A2 (9).

When compared to the LOS from plate-grown strain 2019, the LOS from both the planktonic and the biofilm organisms showed increased heterogeneity (FIG. 12). One factor contributing to the increased heterogeneity is an overall shift to lower phosphorylation states, resulting in a distribution of glycoforms containing 1, 2 or 3 PEAs for each species. In addition to this trend, there is enhanced production of higher molecular weight and sialylated glycoforms in the LOS from planktonic and biofilm organisms, as compared to the LOS from plate-grown strain 2019. These increases are more easily measured when all of the phosphorylation states for a given glycoform are summed and the results for each sample normalized (Table 3).

TABLE 3

Relative abundances of asialo- and sialylated LOS glycoforms in plate-grown, planktonic, and biofilm *H. influenzae* 2019.

| Summed glycoforms | 2019 Plate-grown | 2019 Planktonic | 2019 Biofilm |
|---|---|---|---|
| *Asialoglycoforms* | | | |
| $A_1 + A_2 + A_3$ | 10.0 | 29.2 | 32.5 |
| $B_1 + B_2 + B_3$ | 100 | 100 | 100 |
| $B_{1¶} + B_{2¶} + B_{3¶}$ | 29.2 | — | — |
| $C_1 + C_2 + C_3$ | 22.4 | 63.8 | 118.3 |
| $D_1 + D_2 + D_3$ | 27.7 | 51.5 | 87.8 |
| $E_1 + E_2 + E_3$ | 12.8 | 26.4 | 32.8 |
| $F_1 + F_2$ | — | 7.6 | 18.2 |
| $G_1 + G_2$ | — | 6.8 | 24.6 |
| $H_1 + H_2$ | 16.1 | 35.6 | 31.5 |
| *Sialylated glycoforms* | | | |
| $B_2^* + B_3^*$ | 26.2 | 22.0 | 26.4 |
| $B_1^{} + B_2^{} + B_3^{**}$ | 23.4 | 52.8 | 52.3 |
| $D_1^* + D_2^*$ | 9.0 | 19.0 | 20.6 |
| $D_1^{} + D_2^{}$ | 6.0 | 18.9 | 20.5 |
| $E_1^{} + E_2^{} + E_3^{**}$ | 3.8 | 14.6 | 16.0 |
| $F_2^* + F_3^*$ | 14.5 | 19.0 | 20.4 |
| $H_1^* + H_2^* + H_3^*$ | 11.3 | 20.2 | 41.9 |
| $I_2^* + I_3^*$ | 5.6 | 3.2 | 4.5 |

TABLE 3-continued

Relative abundances of asialo- and sialylated LOS glycoforms in plate-grown, planktonic, and biofilm *H. influenzae* 2019.

| Summed glycoforms | 2019 Plate-grown | 2019 Planktonic | 2019 Biofilm |
|---|---|---|---|
| $I_1^{} + I_2^{} + I_3^{**}$ | 5.3 | 4.2 | 6.1 |
| $I_1^{*} + I_2^{*}$ | 1.7 | 4.4 | 2.6 |

Refer to Table 2 for glycoform compositions. The number of NeuAc, PEA, and ChoP moieties are denoted by asterisks, subscripts, and the "¶" symbol, respectively. Values are normalized to the sum of the "B" glycoforms in each growth condition.

When treated in this semi-quantitative fashion, the MALDI results show increases in glycoforms 'C—H' in the LOS from planktonic and biofilm organisms. These higher molecular weight glycoforms are most abundant in the LOS derived from the biofilm organisms and many of them are acceptors for sialylation. Concomitantly, the overall level of sialylated glycoforms is increased in LOS from planktonic and biofilm organisms, as compared to the LOS from plate-grown strain 2019 (Table 3). In a few cases, individual sialylated glycoforms remained at comparable levels under the three growth conditions. However, most sialylated glycoforms increase 2-fold to 4-fold when LOS is derived from planktonic or biofilm organisms. Such increases are seen for the doubly sialylated LOS glycoforms B, D, and E** of planktonic and biofilm organisms. While in most respects LOS populations from planktonic and biofilm organisms appear quite similar, the H* glycoform appears to be expressed most abundantly in the LOS from biofilm organisms (FIG. 12C and Table 3).

To confirm the assignments of the sialylated glycoforms, portions of the LOS samples from the three growth conditions were treated with immobilized neuraminidase. The MALDI spectrum of the neuraminidase-treated LOS sample from biofilm organisms is shown in FIG. 4D. In all three neuraminidase-treated LOS samples, peaks assigned as sialylated glycoforms were shifted by the loss of one or more NeuAcs.

Figure 13A:
FIGS. 13A, 13B and 13C show confocal images of primary bronchial epithelial cells infected for four days with NTHI 2019::gfp, (FIG. 13A), NTHi 2019rfe::gfp (FIG. 13B) and NTHi 2019lsgG::gfp (FIG. 13C). As can be seen, dense NTHi 2019 biofilm patches covers the epithelial cell surface while only isolated clusters of NTHi 2019rfe::gfp and NTHi 2019lsgG::gfp.
Figure 13B:
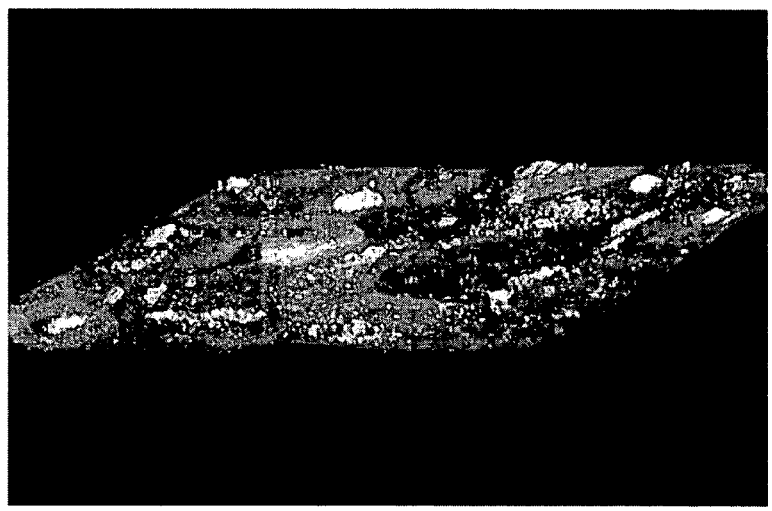
Figure 13C:
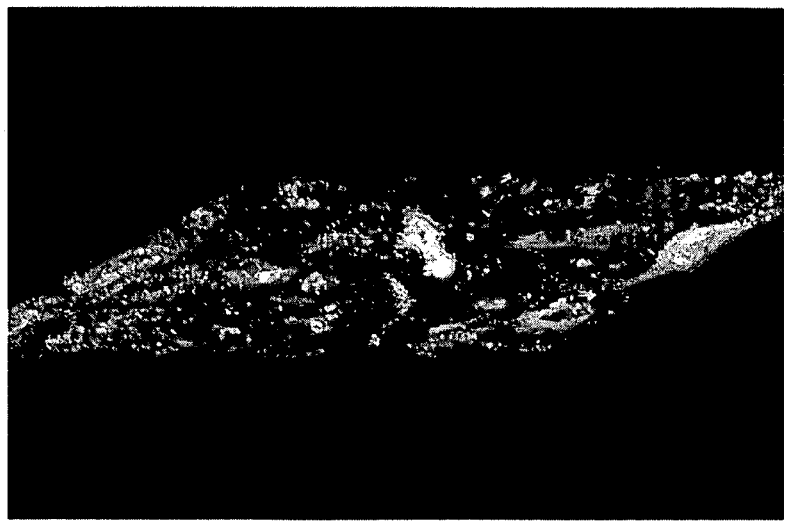
Figure 14A:
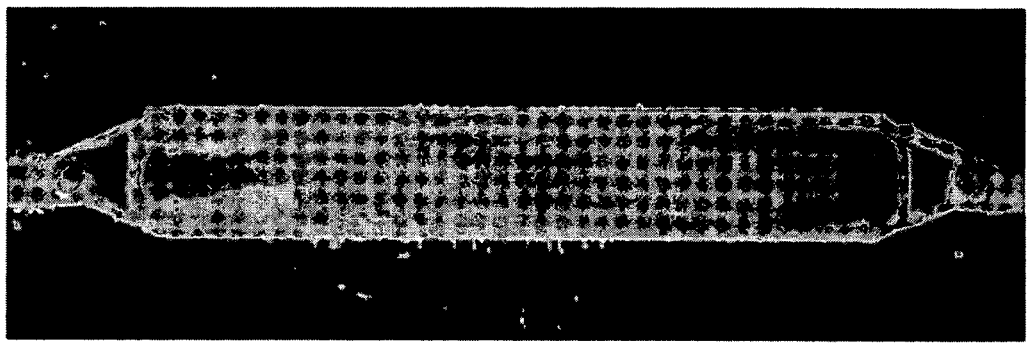
FIGS. 14A and 14B show bioflim formation by NTHi strain 2019 after five days of growth in a continuous flow chamber (FIG. 14A) and a toluidine blue-stained cryosection of the NTHi day five bioflim embedded in OCT (FIG. 14B). The bottom of the section is adjacent to the glass coverslip surface.
Figure 14B:
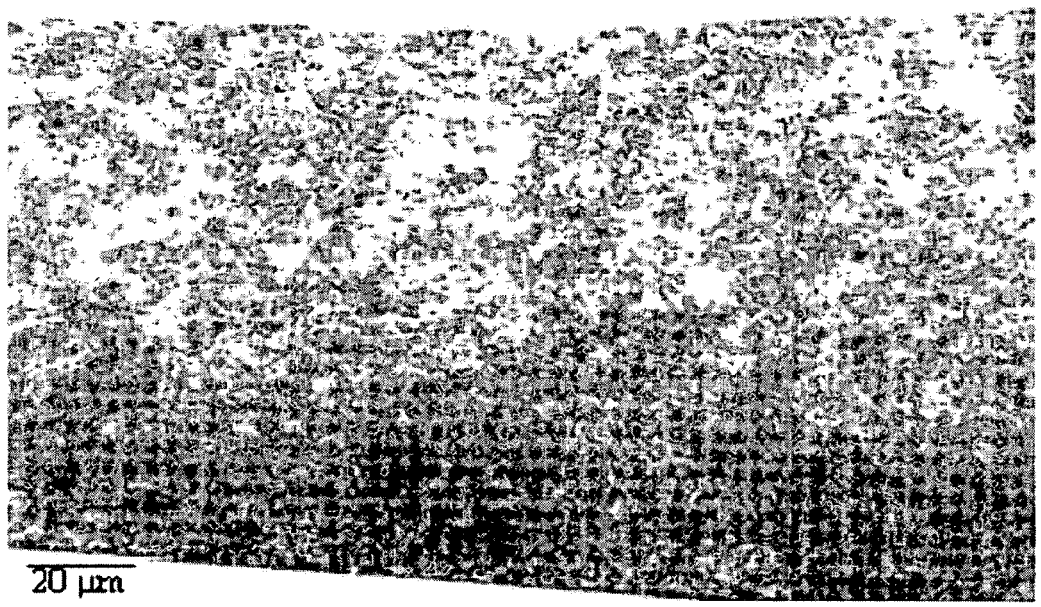
Figure 15A:
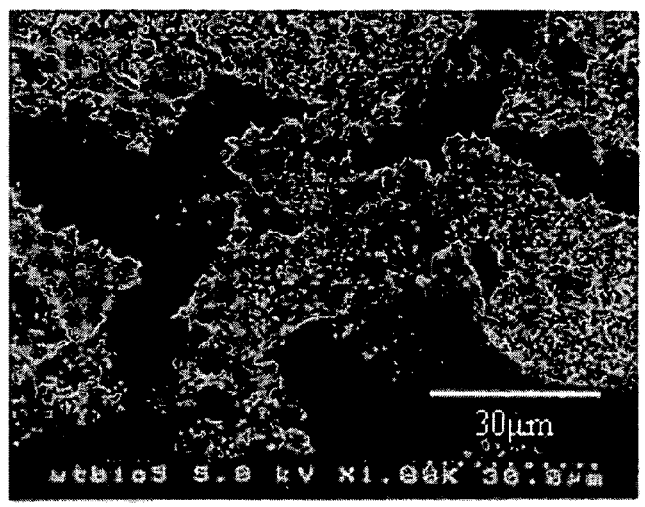
FIGS. 15A, 15B and 15C show scanning electron micrographs of a five-day bioflim.
Figure 15B:
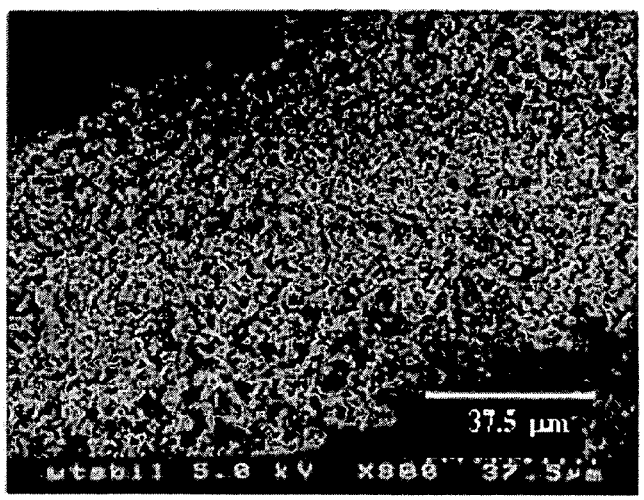
Figure 15C:
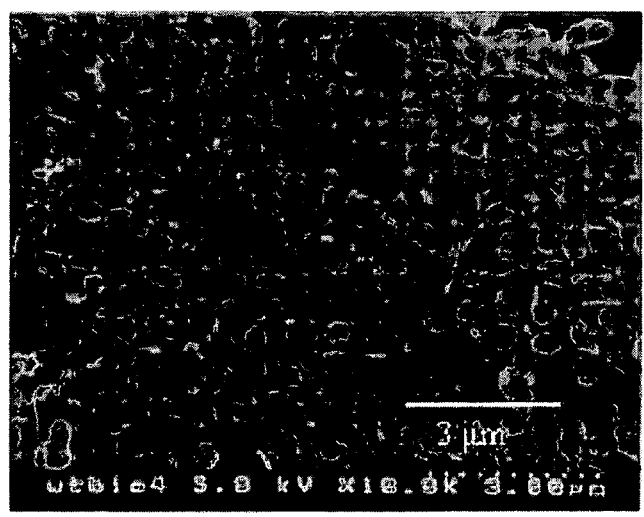

Analysis of NTHi mutants in biofilm formation: In order to determine the role that carbohydrates might play in NTHi biofilm formation, the complex carbohydrate biosynthesis was studied in a group of NTHi 2019 mutants. FIG. 13 shows the results of this study. Seven NTHi 2019 mutants were studied in a microtiter biofilm assay. Interestingly, the mutants, NTHi 2019 galE and NTHi 2019 pgm, formed biofilms. This suggested that glucose, galactose, and mannose were not components of the biofilm matrix. Three of the other mutants, 2019 wecA, 2019 siaB, and 2019 siaA showed a significant reduction in biofilm formation in this assay. Strain 2019 wecA is a mutant in a gene with high homology ($e^{-101}$) to undecaprenyl-phosphate α-N-acetyl-glucosaminyltransferase in *E. coli* K12. Previous studies in our laboratory (unpublished data) and studies of Hood and co-workers (29) indicate that a mutation in this gene does not affect lipooligosaccharide biosynthesis. The microtiter assay suggested that this transferase might be involved in the first step in biofilm biosynthesis, that is, the addition of an initial N-acetylhexosamine to the undecaprenol carrier lipid. Figure panel 14A and panel 14B show confocal analysis of biofilm formation by strain 2019 gfp and 2019 wecA:gfp, respectively, at day 5 in a continuous flow chamber using defined medium. These data confirm the microtiter assay results since essentially no biofilm is form in 2019 wecA while a 50 to 150 micron thick biofilm is formed with NTHi 2019. A similar study was performed with strain 2019 siaB that showed a reduction in the height of the biofilm to 20 to 30 microns at day 5 (FIG. 14C). The O'Toole-Kolter assay also included studies with the three strain 2019 sialyltransferase mutants, lsgB, lic3A, and siaA. A mutation in siaA resulted in significant reduction in biofilm formation in this assay while mutations in lsgB and lic3A did not (FIG. 13). The O'Toole-Kolter and continuous flow studies suggested that NeuAc was an important component of the biofilm. To confirm this observation, biofilm formation was studied in a continuous flow chamber under NeuAc limiting conditions. A chemically defined medium supplemented with NAD and hemin without and with 20 µM NeuAc was perfused through separate chambers infected with NTHi 2019 gfp. These studies showed reduced biofilm formation in the continuous flow chamber perfused with medium without NeuAc supplementation (FIGS. 14D and 14E). Similar results were obtained with the biofilm microtiter assay (FIG. 15A). In order to confirm that NeuAc was incorporated into biofilm produced by NTHi 2019 pgm, $^{14}$C NeuAc uptake studies were performed. These studies were performed with strains NTHi 2019 nanA and NTHi 2019 nanA::pgm. *H. influenzae* cannot synthesize sialic acid but it can degrade sialic acid to N-acetylmannosamine by the action of N-acetylneuraminate lysase (NanA). FIG. 15B shows that NTHi 2019 nanA::pgm incorporates $^{14}$C NeuAc into biofilm as efficiently as NTHi 2019 nanA does into biofilm and LOS.

Figure 16A:
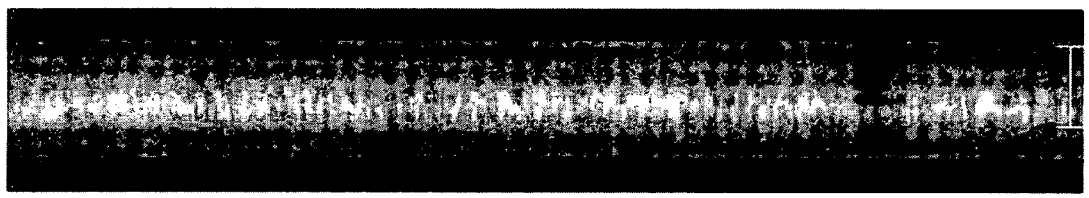
FIGS. 16A and 16B show the results of confocal microscopy of live/dead staining of the biofilm at day 2 (FIG. 16A) and day 5 (FIG. 16B). The panels are presented as vertical sections of a Z-series comprised of 10-five micron optical sections. The biofilms are embedded in OCT and were cryosectioned. Viable organisms can be seen in each specimen; however, by five days a greater proportion of the organisms at the coverslip surface appear to be non-viable, based on this assay. The scale bars represent 100 µm.
Figure 16B:
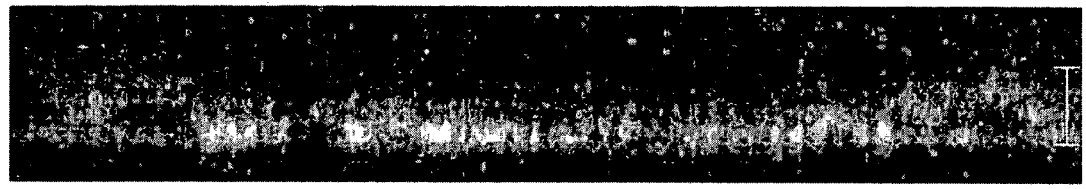
Figure 17:
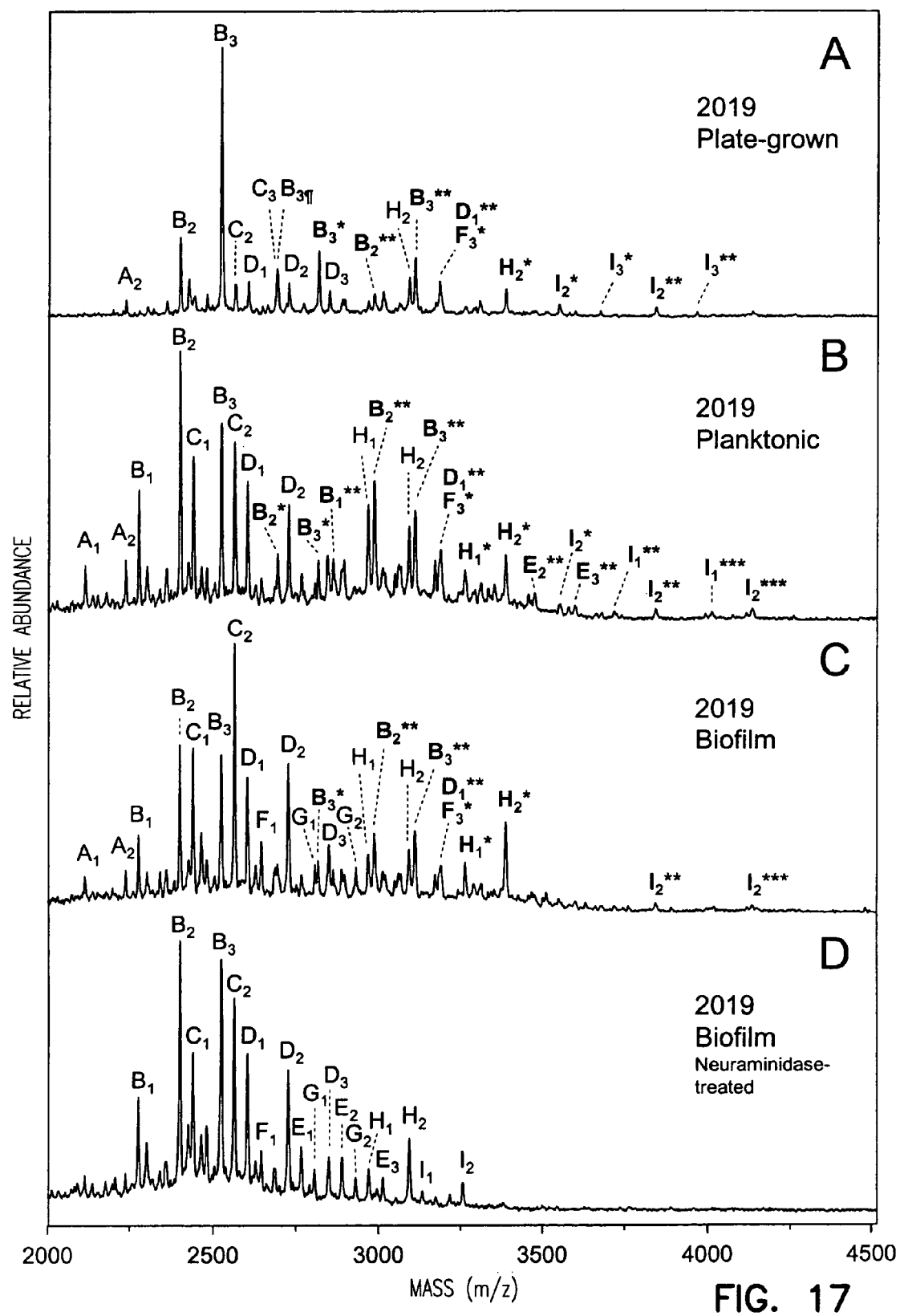
FIGS. 17A, 17B, 17C and 17D show mass spectrometry analysis of NTHi 2019 LOS isolated from plate-grown (FIG. 17A), day five biofilm (FIG. 17C), day five planktonic organisms (FIG. 17B), and neuraminidase-treated biofilm (FIG. 17D). Sialylated glycoforms are designated in red. A completed description of the spectra is given in the text and Tables 2 and 3.
Figure 18:
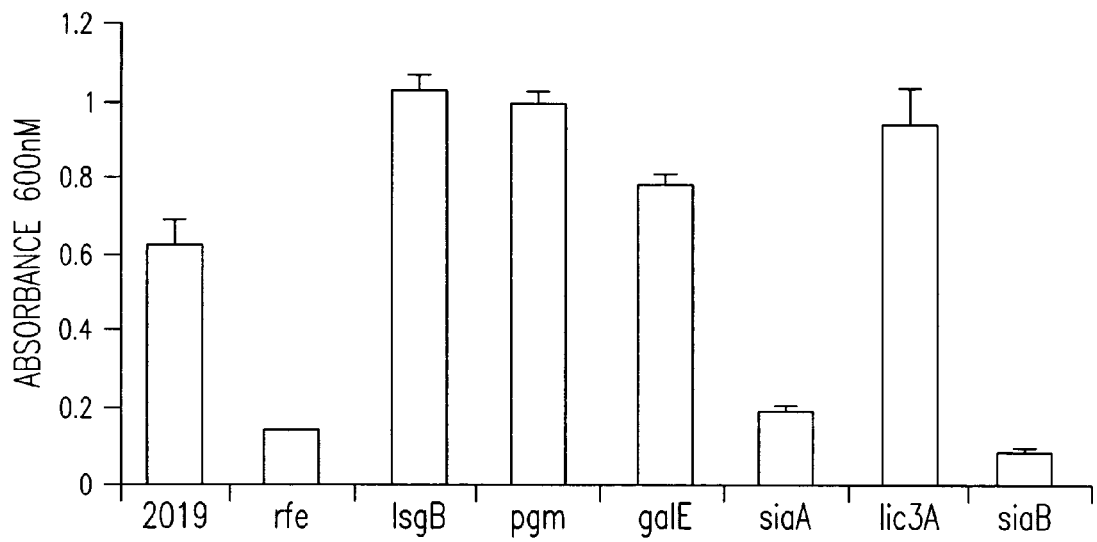
FIG. 18. Results of O'Toole-Kolter assays of strain 2019 and eight 2019 mutants are shown in FIG. 18. As can be seen, three mutants, siaA, siaB, and wecA, produced significantly less biofilm than the parent strain. The other mutants produced biofilm in amounts similar to or greater than the parent strain.
Figure 19A:
FIGS. 19A, 19B, 19C, 19D, and 19E show vertical cross-sections comprised of 60 one micron optical sections of confocal microscopic studies of day five continuous flow chambers infected with NTHi 2019 gfp (FIG. 19A), NTHi 2019 wecA::gfp (FIG. 19B), NTHi 2019 siaB::gfp (FIG. 19C), NTHi 2019 gfp in medium without NeuAc supplementation (FIG. 19E) and NTHi 2019 gfp in medium supplemented with 20 µg/ml NeuAc supplementation (FIG. 19D).
Figure 19B:
Figure 19C:
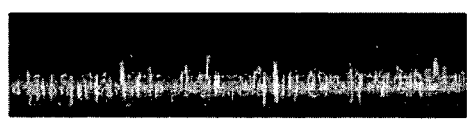
Figure 19D:
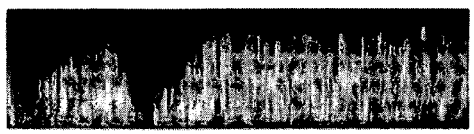
Figure 19E:
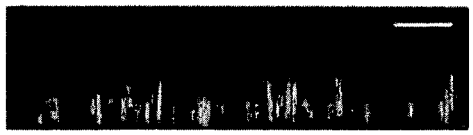
Figure 20A:
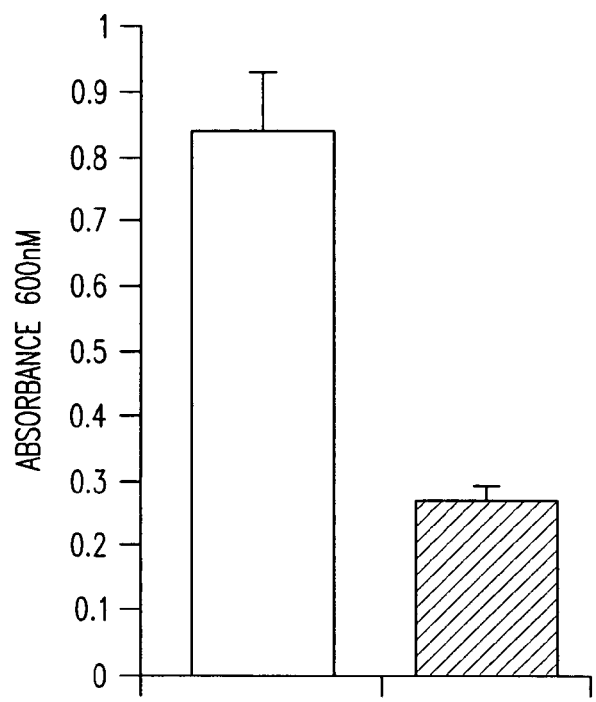
FIGS. 20A and 20B show O'Toole-Kolter assays demonstrating the reduction of biofilm when NTHi 2019 is grown in defined medium with (■) and without NeuAc (▨) supplementation is seen in FIG. 20A. Each result is a mean result from of eight wells. The bars represent one standard deviation. The difference in biofilm between growth in 20 µM NeuAc and NeuAc-free media is significant ($p<0.005$).
Figure 20B:
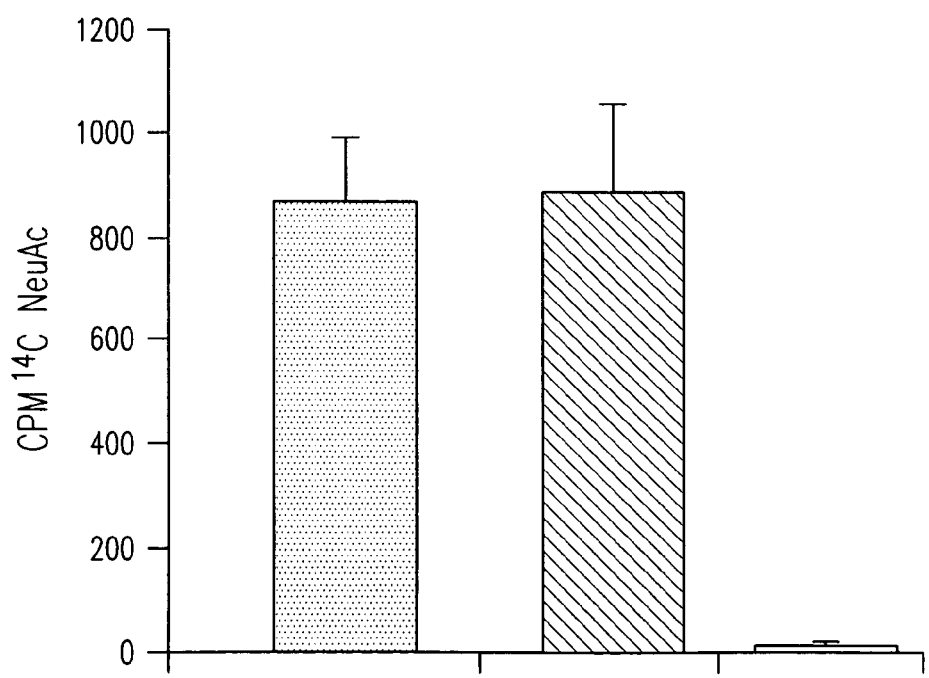
Figure 21A:
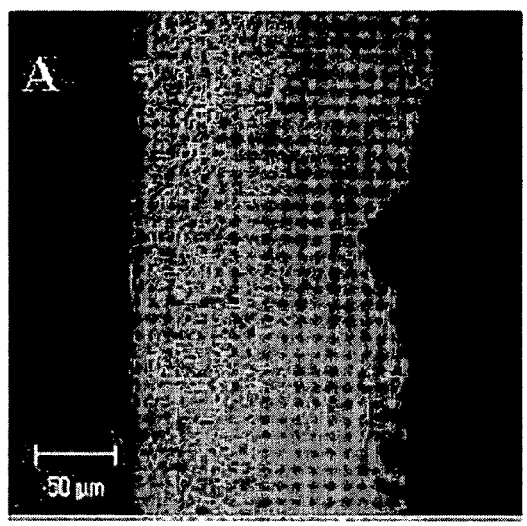
FIGS. 21A, 21B and 21C show a confocal micrograph of OCT-embedded cryosectioned biofilm stained with *Sambucus nigrans*-TRITC (FIG. 21A) and *Mauchia amurensis*-FITC (FIG. 21B). The merged image of panel A and B is shown in (FIG. 21C).
Figure 21B:
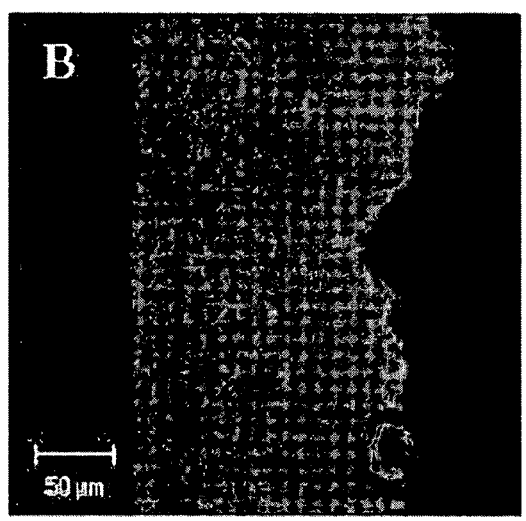
Figure 21C:
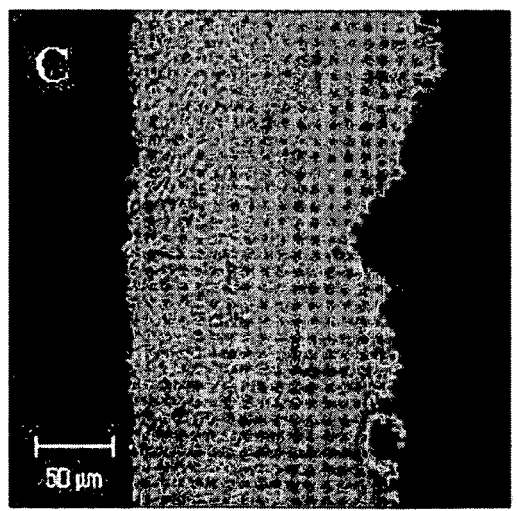
Figure 22A:
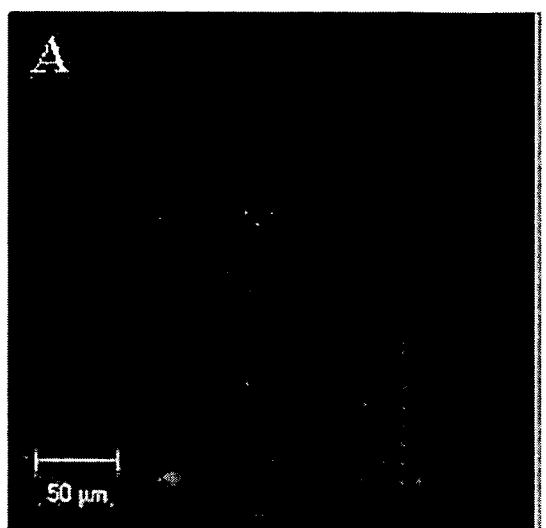
FIGS. 22A, 22B and 22C show a confocal micrograph of OCT-embedded cryosectioned biofilm stained with *Sambucus nigrans*-TRITC (FIG. 22A) and *Maachia amurensis*-FITC (FIG. 22B) after 1 hour exposure to 0.05 units of *Vibrio cholera* neuraminidase. The merged image of panels A and B is shown in (FIG. 22C). The scale bars represent 50 µm.
Figure 22B:
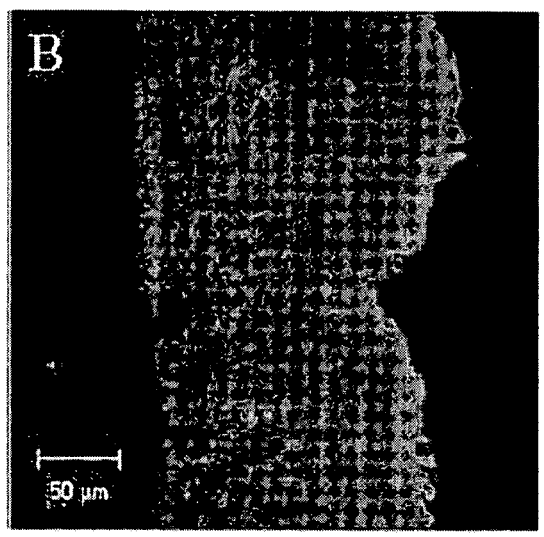
Figure 22C:
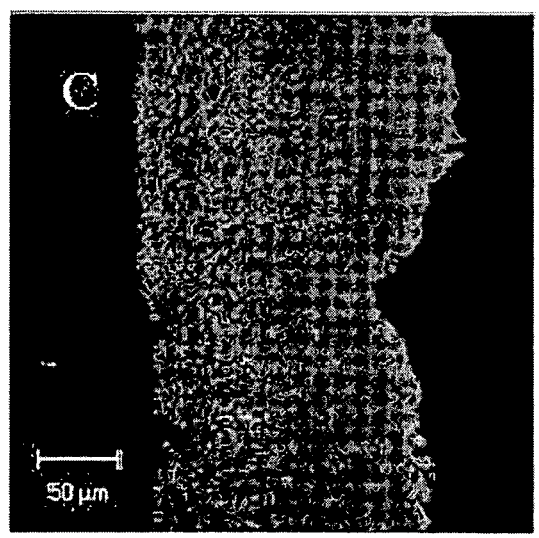

Analysis of biofilm composition by lectin binding studies: In order to confirm that NeuAc was a component of the biofilm, OCT embedded strain 2019 pgm biofilm was studied with the *Maachia amurensis* and *Sambucus nigra* lectins conjugated to fluorescein and texas red isothiocyanate, respectively. *Maachia amurensis* lectin binds preferentially to a terminal NeuAc α2→3Gal, and *Sambucus nigra* lectin binds preferentially to terminal NeuAc α2→6Gal. To avoid possible binding of these lectins to the NeuAc on NTHi LOS 2019 pgm biofilm was studied in these experiments. This mutant makes an LOS that is severely truncated and lacks acceptors for NeuAc. Thus, any NeuAc detected in studies of 2019 pgm biofilm with these lectins would be present only in the biofilm matrix. The 2019 pgm biofilm was collected after 5 days of growth in the continuous flow chamber and embedded in OCT. FIGS. 16A and 16B shows the results of microscopic analysis of staining with these lectins before and after treatment of the biofilm with sialidase. *Sambucus nigra*-TRITC bound strongly to the biofilm while *Maachia amurensis*-FITC gave a much less intense signal. After sialidase treatment, *Sambucus nigra* lectin no longer bound to the biofilm. In addition, *Sambucus nigra*-TRITC binding to the biofilm could be inhibited by preincubation with α2→6 N-acetylneuramyl-lactose (data not shown). There was no change in binding with *Maachia amurensis*-FITC after sialidase treatment, suggesting that the binding of this lectin was not to sialic acid and that the *Maachia amurensis*-FITC binding was either non-specific or to another component of the biofilm. These studies suggest that NeuAc is present in the 2019 pgm biofilm in an α2→6 linkage.

Discussion

Biofilms are complex communities of microorganisms that develop on surfaces in diverse environments (30). They are found in many differing environments including industrial pipelines, ventilation systems, catheters, and medical implants. They are involved in disease in both humans and animals. Biofilms are dynamic structures, which start by the attachment of bacteria to a surface, development of microcolonies, followed by the development of the mature, structurally complex biofilm (30). Bacteria eventually detach from the mature and enter the surrounding fluid phase, becoming planktonic organisms that can then repeat the process on other parts of the surface.

Mechanisms involved in the initial attachment differ among microorganisms. The initiation of a biofilm can occur in one of three ways. The first is by the redistribution of attached cells by surface motility. O'Toole and Kolter (31) demonstrate that the type IV pili of *Pseudomonas aeruginosa* play an important role in surface adherence. The second mechanism in which biofilm formation can occur is from the binary division of attached cells (32). The third and final mechanism is the recruitment of bacterial cells from the surrounding media (33).

Once initial attachment has been made, the cells must convert from reversible attachment to irreversible attachment, in which the cells switch from a weak interaction with the substratum to a permanent bonding through extracellular polymers. In addition to the formation of the exopolymers, the bacteria form channels and pores and redistribute away from the substratum (34).

The maintenance of a biofilm is attributed to the development and maintenance of the exopolysaccharide matix (35). More than 300 proteins can be detected in bacteria from mature biofilms and not in planktonic bacteria (36). These proteins fall into the classes of metabolism, phospholipid and LPS-biosynthesis, membrane transport and secretion, and adaptation and protective mechanisms. In addition, biofilm bacteria are considered to be in the stationary-phase partly due to the accumulation of acylhomoserine lactone within clusters (37).

Detachment is a physiologically regulated event in which bacteria will release from the biofilm as a planktonic organism to move on to attach to other surfaces. Many different mechanisms may contribute to the detachment process. O'Toole and Kolter (31) demonstrate that starvation may lead to detachment by an unknown mechanism. *Steptococcus mutans* produces a surface protein-releasing enzyme that mediates the release of cells from biofilms (38). A possible trigger for the release of the matrix-degrading enzyme could be cell density. In addition, the presence of homoserine lactones may cause the reduction of biofilm, as demonstrated with *Rhodobacter sphaeroides* (31,39).

In *P. aeruginosa*, flagella and type IV pili-mediated twitching-motility play important roles in surface aggregation (31). In *E. coli*, flagella, type I pili, and curli fimbrae have been implicated in biofilm formation (40). Motility is not absolutely necessary as many non-motile bacteria such as *Staphylococcus epidermidis* and *S. mutans* can also form biofilms. The microbes within the biofilm undergo changes in gene expression when compared to plate-grown or planktonic bacteria (17). It is demonstrated that *Pseudomonas putida* undergoes phenotypic changes in protein expression such that different stages of biofilm development can be recognized (36).

Recent studies provide evidence that *H. influenzae* can produce a biofilm during otitis media in humans and in the chinchilla middle ear during experimental otitis media. Murphy and Kickham (10) demonstrate that *H. influenzae* pili may play a role during growth in the O'Toole-Kolter microtiter plate assay. NTHi 2019 can form a biofilm in the O'Toole-Kolter assay as well as in a continuous flow system. As disclosed herein, these systems were used to identify genes involved in the formation of the extracellular polymeric substances (EPS) of the NTHi 2019 biofilm. These studies have shown that undecaprenol, 2019 siaB, and 2019 siaA are involved in the formation of the NTHi 2019 EPS.

NTHi 2019 wecA has high homology to the same gene in *E. coli, Yersinia pestis*, and *Salmonella typhimurium* (e value<$e^{-100}$). Previous studies indicate that it plays no role in *H. influenzae* LOS biosynthesis (29,41,42). This gene encodes for undecaprenyl-phosphate α-N-acetyl-glucosaminyl-transferase, and homologs are shown to be involved in the initial step in enterobacterial common antigen (41-43) and O-antigen biosynthesis in *Salmonella enterica* serovar Borreze (44) and *P. aeruginosa* (45). *S. mutans* rgpG, which has homology to *E. coli* wecA, is involved in the biosynthesis of an extracellular polysaccharide (46). We have demonstrated in the O'Toole-Kolter assay and in a continuous flow chamber using NTHi 2019 wecA::gfp that no biofilm is produced by this mutant. This suggests that NTHi wecA is involved in the initial step in biosynthesis of the biofilm and that the biofilm is synthesized on undecaprenol pyrophosphate.

NTHi SiaB is a CMP-NeuAc synthetase (47), and NTHi SiaA is a sialytranferase. Mutation of either NTHi 2019 siaB or NTHi 2019 siaA (47) resulted in significantly reduced biofilm production in both the O'Toole-Kolter assay and in continuous flow chambers. Compared to NTHi 2019 weca, in which no biofilm formed by five days, a small but detectable biofilm could be seen in the continuous flow chamber with these mutants. NTHi has two other sialyltransferase, Lic3A and LsgB (23,47), and mutations in neither of these sialyltransferases altered NTHi 2019 biofilm formation. When *H. influenzae* lsgB and lic3A are mutated, SiaA can sialylate *H. influenzae* LOS; however, its primary role most probably is involvement in biofilm formation (9).

The NTHi 2019 pgm mutant can make a biofilm equivalent to or greater than the parent strain. This would indicate that glucose and galactose are probably not a component of the NTHi biofilm, as this gene encodes for an enzyme essential to the biosynthesis of nucleotide derivatives of these sugars. The formation of a NeuAc containing biofilm by NTHi 2019 pgm indicates that the terminal acceptor for the NeuAc is most likely a hexosamine, most probably N-acetylgalactosamine.

The binding of *Macchia ameurensis* and *Sambucus nigra* lectins, to the NTHi 2019 pgm biofilm was studied. In these experiments, the biofilm produced by this mutant was used because it does not produce an LOS with an acceptor for sialylation. This allowed the study of NeuAc expression on the biofilm alone. Studies using the *Sambucus nigra* lectin, before and after *V. cholera* neuraminidase treatment, gave further evidence that NeuAc is the terminal sugar in the biofilm. *Macchia ameurensis* lectin binds preferentially to NeuAc in an α(2-3) linkage (48) while *Sambuca nigrans* lectin binds preferentially to NeuAc in an α(2-6) linkage (49). The binding of *Sambucus nigra* lectin combined with the failure of *Macchia ameurensis* lectin to bind to the NTHi 2019 pgm biofilm suggested that the NeuAc is incorporated via an α(2-6) linkage.

NTHi LOS undergo significant changes from the plate grow organisms to both the biofilm and planktonic bacteria. The biofilm and planktonic LOS becomes more heterogeneous. Sialylated, disialylated, and polysialylated species can be found. In general, most of the sialylated glycoforms increased two- to four-fold in LOS isolated from biofilm or planktonic organisms. This is especially true of the double sialylated glycoforns. There is also a shift to a lower phosphorylation state in the biofilm and planktonic LOS. Specific differences also existed between biofilm and planktonic LOS with the abundance of specific glycoforms increased in each.

NTHi cannot synthesize NeuAc and obtains it from its environment. Recent studies in a chinchilla middle ear infection have suggested that NeuAc incorporation into LOS is necessary for pathogenicity (50). These adaptations would enhance survival within the host environment.

BIBILIOGRAPHY

1. Miller, M. B., and Bassler, B. L. (2001) *Annu Rev Microbiol* 55, 165-199
2. Bluestone, C. D. (1982) *N Engl J Med* 306, 1399-1404
3. Murphy, T. F., and Apicella, M. A. (1987) *Rev. Infect. Dis.* 9, 1-15
4. Ehrlich, G. D., Veeh, R., Wang, X., Costerton, J. W., Hayes, J. D., Hu, F. Z., Daigle, B. J., Ehrlich, M. D., and Post, J. C. (2002) *Jama* 287, 1710-1715
5. Campagnari, A. A., Gupta, M. R., Dudas, K. C., Murphy, T. F., and Apicella, M. A. (1987) *Infect. Immun.* 55, 882-887
6. Barcak, G. J., Tomb, J.-F., Laufer, C. S., and Smith, H. O. (1989) *Journal of Bacteriology* 171, 2451-2457
7. Williams, P., Hung, W. L., and Redfield, R. J. (1996) *FEMS Microbiol Lett* 137, 183-187
8. Fleischmann, R. D., Adams, M. D., White, O., Clayton, R. A., Kirkness, E. F., Kerlavage, A. R., Bult, C. J., Tomb, J.-F., Dougherty, B. A., Merrick, J. M., McKenney, K., Sutton, G., FitzHugh, W., Fields, C., Gocayne, J. D., Scott, J., Shirley, R., Liu, L.-I., Glodek, A., Kelley, J. M., Weidman, J. F., Phillips, C. A., Spriggs, T., Hedblom, E., Cotton, M. D., Utterback, T. R., Hanna, M. C., Nguyen, D. T., Saudek, D. M., Brandon, R. C., Fine, L. D., Fritchman, J. L., Fuhrmann, J. L., Geoghagen, N. S. M., Gnehm, C. L., McDonald, L. A., Small, K. V., Fraser, C. M., Smith, H. O., and Venter, J. C. (1995) *Science* 269, 496-512
9. Jones, P. A., Samuels, N. M., Phillips, N. J., Munson, R. S., Jr., Bozue, J. A., Arseneau, J. A., Nichols, W. A., Zaleski, A., Gibson, B. W., and Apicella, M. A. (2002) *J Biol Chem* 277, 14598-14611
10. Murphy, T. F., and Kirkham, C. (2002) *BMC Microbiol* 2, 7
11. O'Toole, G. A., and Kolter, R. (1998) *Mol Microbiol* 28, 449-461
12. Singh, P. K., Parsek, M. R., Greenberg, E. P., and Welsh, M. J. (2002) *Nature* 417, 552-555
13. Morse, S. A., Mintz, C. S., Sarafian, S. K., Barenstein, L., Bertram, B., and Apicella, M. A. (1983) *Infect. Immun.* 41, 74-82
14. Edwards, J. L., Shao, J. Q., Ault, K. A., and Apicella, M. A. (2000) *Infect Immun* 68, 5354-5363.

15. Hitchcock, P. J., and Brown, T. M. (1983) *J. Bacteriol.* 154, 269-277
16. Gibson, B. W., Engstrom, J. J., John, C. M., Hines, W., and Falick, A. M. (1997) *J. Am. Soc. Mass Spectrom.* 8, 645-658
17. Whiteley, M., Bangera, M. G., Bumgarner, R. E., Parsek, M. R., Teitzel, G. M., Lory, S., and Greenberg, E. P. (2001) *Nature* 413, 860-864
18. Phillips, N. J., Apicella, M. A., Griffiss, J. M., and Gibson, B. W. (1992) *Biochemistry* 31, 4515-4526
19. Gaucher, S. P., Cancilla, M. T., Phillips, N. J., Gibson, B. W., and Leary, J. A. (2000) *Biochemistry* 39, 12406-12414
20. Schweda, E. K., Hegedus, O. E., Borrelli, S., Lindberg, A. A., Weiser, J. N., Maskell, D. J., and Moxon, E. R. (1993) *Carbohydr Res* 246, 319-330
21. Masoud, H., Moxon, E. R., Martin, A., Krajcarski, D., and Richards, J. C. (1997) *Biochemistry* 36, 2091-2103
22. Mansson, M., Hood, D. W., Li, J., Richards, J. C., Moxon, E. R., and Schweda, E. K. (2002) *Eur J Biochem* 269, 808-818
23. Hood, D. W., Makepeace, K., Deadman, M. E., Rest, R. F., Thibault, P., Martin, A., Richards, J. C., and Moxon, E. R. (1999) *Mol Microbiol* 33, 679-692
24. Schweda, E. K., Li, J., Moxon, E. R., and Richards, J. C. (2002) *Carbohydr Res* 337, 409-420
25. Schweda, E. K., Brisson, J. R., Alvelius, G., Martin, A., Weiser, J. N., Hood, D. W., Moxon, E. R., and Richards, J. C. (2000) *Eur J Biochem* 267, 3902-3913
26. Mansson, M., Bauer, S. H., Hood, D. W., Richards, J. C., Moxon, E. R., and Schweda, E. K. (2001) *Eur J Biochem* 268, 2148-2159
27. Cox, A. D., Hood, D. W., Martin, A., Makepeace, K. M., Deadman, M. E., Li, J., Brisson, J. R., Moxon, E. R., and Richards, J. C. (2002) *Eur J Biochem* 269, 4009-4019
28. Phillips, N. J., Apicella, M. A., Griffiss, J. M., and Gibson, B. W. (1993) *Biochemistry* 32, 2003-2012
29. Hood, D., Deadman, M., Allen, T., Masoud, H., Martin, A., Brisson, J., Fleischmann, R., Venter, J., Richards, J., and Moxon, E. R. (1996) *Molecular Microbiology* 22, 951-965
30. Hall-Stoodley, L., and Stoodley, P. (2002) *Curr Opin Biotechnol* 13, 228-233
31. O'Toole, G. A., and Kolter, R. (1998) *Mol Microbiol* 30, 295-304
32. Heydorn, A., Nielsen, A. T., Hentzer, M., Sternberg, C., Givskov, M., Ersboll, B. K., and Molin, S. (2000) *Microbiology* 146 (Pt 10), 2395-2407
33. Tolker-Nielsen, T., Brinch, U. C., Ragas, P. C., Andersen, J. B., Jacobsen, C. S., and Molin, S. (2000) *J Bacteriol* 182, 6482-6489
34. Davies, D. G., and Geesey, G. G. (1995) *Appl Environ Microbiol* 61, 860-867
35. Davies, D. G., Chakrabarty, A. M., and Geesey, G. G. (1993) *Appl Environ Microbiol* 59, 1181-1186
36. Sauer, K., Camper, A. K., Ehrlich, G. D., Costerton, J. W., and Davies, D. G. (2002) *J Bacteriol* 184, 1140-1154
37. Stoodley, P., Sauer, K., Davies, D. G., and Costerton, J. W. (2002) *Annu Rev Microbiol* 56, 187-209
38. Lee, S. F., Li, Y. H., and Bowden, G. H. (1996) *Infect Immun* 64, 1035-1038
39. Puskas, A., Greenberg, E. P., Kaplan, S., and Schaefer, A. L. (1997) *J Bacteriol* 179, 7530-7537
40. Jackson, D. W., Suzuki, K., Oakford, L., Simecka, J. W., Hart, M. E., and Romeo, T. (2002) *J Bacteriol* 184, 290-301
41. Meier-Dieter, U., Barr, K., Starman, R., Hatch, L., and Rick, P. D. (1992) *The Journal of Biological Chemistry* 267, 746-753
42. Meier-Dieter, U., Starman, R., Barr, K., Mayer, H., and Rick, P. D. (1990) *The Journal of Biological Chemistry* 265, 13490-13497
43. Ohta, M., Ina, K., Kusuzaki, K., Kido, N., Arakawa, Y., and Kato, N. (1991) *Mol Microbiol* 5, 1853-1862
44. Keenleyside, W. J., Perry, M., Maclean, L., Poppe, C., and Whitfield, C. (1994) *Mol Microbiol* 11, 437-448
45. Burrows, L. L., and Lam, J. S. (1999) *J Bacteriol* 181, 973-980
46. Shibata, Y., Yamashita, Y., Ozaki, K., Nakano, Y., and Koga, T. (2002) *Infect Immun* 70, 2891-2898
47. Jones, P. A., Samuels, N. M., Phillips, N. J., Munson, R. S., Jr., Bozue, J. A., Arseneau, J. A., Nichols, W. A., Zaleski, A., Gibson, B. W., and Apicella, M. A. (2002) *J Biol Chem* 277
48. Wang, W. C., and Cummings, R. D. (1988) *J Biol Chem* 263, 4576-4585
49. Shibuya, N., Goldstein, I. J., Broekaert, W. F., Nsimba-Lubaki, M., Peeters, B., and Peumans, W. J. (1987) *J Biol Chem* 262, 1596-1601
50. Bouchet, V., Hood, D. W., Li, J., Brisson, J. R., Randle, G. A., Martin, A., Li, Z., Goldstein, R., Schweda, E. K., Pelton, S. I., Richards, J. C., and Moxon, E. R. (2003) *Proc Natl Acad Sci USA* 100, 8898-8903
51. Maskell, D. J., Szabo, M. J., Deadman, M. E., and Moxon, E. R. (1992) *Mol. Microbiol.* 6, 3051-3063
52. Hood, D. W., Cox, A. D., Gilbert, M., Makepeace, K., Walsh, S., Deadman, M. E., Cody, A., Martin, A., Mansson, M., Schweda, E. K., Brisson, J. R., Richards, J. C., Moxon, E. R., and Wakarchuk, W. W. (2001) *Mol Microbiol* 39, 341-350.
53. Swords, W. E., Buscher, B. A., Ver Steeg Ii, K., Preston, A., Nichols, W. A., Weiser, J. N., Gibson, B. W., and Apicella, M. A. (2000) *Mol Microbiol* 37, 13-27.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An isolated and purified mutant *Haemophilus influenzae* cell comprising a mutant LsgG gene containing an insertion, substitution or deletion as compared to a wild-type LsgG gene, wherein said insertion, substitution or deletion results in a *Haemophilus influenzae* cell which has a reduced biofilm formation ability as compared to a wild-type *Haemophilus influenzae* cell.

2. The isolated and purified mutant *Haemophilus influenzae* cell of claim 1, wherein the LsgG gene is disrupted by insertional inactivation.

3. The isolated and purified mutant *Haemophilus influenzae* cell of claim 1, further comprising a mutant Rfe gene containing an insertion, substitution or deletion as compared to a wild-type Rfe gene, wherein said insertion, substitution or deletion renders said mutant cell incapable of producing a homolog of undecaprenyl-phosphate alpha-N-acetylglucosaminyltransferase, which is involved in the addition of the first sugar to the carrier lipid upon which a biofilm is assembled in non-typeable *Haemophilus influenzae*.

4. A composition comprising the isolated and purified mutant *Haemophilus influenzae* cell of claim 1 in combination with a physiologically acceptable, non-toxic vehicle.

5. The composition of claim 4, which further comprises an effective amount of an immunological adjuvant.

* * * * *

SEQUENCE LISTING

<160> NUMBER OF SEQ ID NOS: 8

<210> SEQ ID NO 1
<211> LENGTH: 255
<212> TYPE: PRT

<213> ORGANISM: Haemophilus influenzae

<400> SEQUENCE: 1

```
Met Lys Asn Thr Glu Ile Leu Leu Thr Ile Lys Leu Gln Gln Ala Leu
 1               5                  10                  15
Phe Ile Asp Pro Lys Arg Val Arg Leu Leu Lys Glu Ile Gln Gln Cys
            20                  25                  30
Gly Ser Ile Asn Gln Ala Ala Lys Asn Ala Lys Val Ser Tyr Lys Ser
        35                  40                  45
Ala Trp Asp His Leu Glu Ala Met Asn Lys Ile Ser Pro Arg Pro Leu
 50                  55                  60
Leu Glu Arg Asn Thr Gly Gly Lys Asn Gly Gly Thr Ala Leu Thr
 65                  70                  75                  80
Thr Tyr Ala Glu Arg Leu Leu Gln Leu Tyr Asp Leu Leu Glu Arg Thr
                85                  90                  95
Gln Glu His Ala Phe His Ile Leu Gln Asp Glu Ser Val Pro Leu Asp
            100                 105                 110
Ser Leu Leu Thr Ala Thr Ala Arg Phe Ser Leu Gln Ser Ser Ala Arg
        115                 120                 125
Asn Gln Phe Phe Gly Arg Val Ala Gln Gln Arg Ile Ile Asp Ser Arg
130                 135                 140
Cys Val Val Asp Val Asn Val Gln Gly Leu Pro Thr Pro Leu Gln Val
145                 150                 155                 160
Ser Ile Thr Thr Lys Ser Ser Ala Arg Leu Lys Leu Ile Thr Glu Lys
                165                 170                 175
Glu Val Met Leu Met Phe Lys Ala Pro Trp Val Lys Ile Ser Glu Gln
            180                 185                 190
Pro Leu Ala Asn Gln Pro Asn Gln Phe Pro Val Asn Ile Lys Ser Leu
        195                 200                 205
Asn Glu Glu Ala Ile Leu Gln Phe Ala Glu Ser Asn Ile Glu Phe
210                 215                 220
Cys Ala Thr Val His Gln Pro Asn Gln Trp Gln Ile Glu Gln Gln Val
225                 230                 235                 240
Trp Ile His Ile Asp Gln Glu Gln Ile Ile Leu Ala Thr Leu Gly
                245                 250                 255
```

<210> SEQ ID NO 2
<211> LENGTH: 765
<212> TYPE: DNA
<213> ORGANISM: Haemophilus influenzae

<400> SEQUENCE: 2

```
atgaaaaaca ccgaaatttt actcaccatt aaacttcaac aagcactttt tatcgatcca    60
aaacgagttc gtttactcaa agaaattcaa caatgcggtt caattaatca agctgcgaaa   120
aatgccaaag tgagctataa agtgcgtgg gatcatttag aagccatgaa taaaatcagc   180
cctcgcccat tgctggaacg aaatacaggt ggaaaaaatg gcggaggcac ggcacttact   240
acttatgccg agcgttttgct ccaactttat gatttattag aacgtacgca agaacacgcg   300
tttcatattc tacaagatga atccgtaccg ttagatagtt tactcacggc aaccgcacgt   360
ttttctttac aaagtagcgc acgcaatcaa tttttttgggc gagtggcaca acaacgcatt   420
attgactctc gttgcgttgt ggatgtgaat gtgcaaggat taccaacgcc attgcaagtt   480
tctattacca caaaaagctc ggctcgtttg aaactcatta cggaaaaaga agtgatgctg   540
atgttcaagg ctccttgggt aaaaatcagt gaacaaccat tagcaaatca accgaatcag   600
```

```
ttccccgtaa atatcaaatc actcaatgaa gaggaagcca tccttcaatt tgctgaaagc      660
aacattgaat tttgtgccac agtccaccag ccaaatcaat ggcaaatcga gcaacaggtt      720
tggattcaca ttgatcaaga gcaaattatt ttagcgacgc tgggg                      765

<210> SEQ ID NO 3
<211> LENGTH: 355
<212> TYPE: PRT
<213> ORGANISM: Haemophilus influenzae

<400> SEQUENCE: 3

Met Leu Ser Ile Phe Val Thr Phe Leu Gly Ala Phe Leu Thr Leu Ile
 1               5                  10                  15

Val Met Arg Pro Leu Ala Asn Trp Ile Gly Leu Val Asp Lys Pro Asn
            20                  25                  30

Tyr Arg Lys Arg His Gln Gly Thr Ile Pro Leu Ile Gly Gly Ala Ser
        35                  40                  45

Leu Phe Val Gly Asn Leu Cys Tyr Tyr Leu Met Glu Trp Asp Gln Leu
    50                  55                  60

Arg Leu Pro Tyr Leu Tyr Leu Phe Ser Ile Phe Val Leu Leu Ala Ile
65                  70                  75                  80

Gly Ile Leu Asp Asp Arg Phe Asp Ile Ser Pro Phe Leu Arg Ala Gly
                85                  90                  95

Ile Gln Ala Ile Leu Ala Ile Leu Met Ile Asp Leu Gly Asn Ile Tyr
            100                 105                 110

Leu Asp His Leu Gly Gln Ile Leu Gly Pro Phe Gln Leu Thr Leu Gly
        115                 120                 125

Ser Ile Gly Leu Ile Ile Thr Val Phe Ala Thr Ile Ala Ile Ile Asn
    130                 135                 140

Ala Phe Asn Met Ile Asp Gly Ile Asp Gly Leu Leu Gly Gly Leu Ser
145                 150                 155                 160

Cys Val Ser Phe Ala Ala Ile Gly Ile Leu Met Tyr Arg Asp Gly Gln
                165                 170                 175

Met Asp Met Ala His Trp Ser Phe Ala Leu Ile Val Ser Ile Leu Pro
            180                 185                 190

Tyr Leu Met Leu Asn Leu Gly Ile Pro Phe Gly Pro Lys Tyr Lys Val
        195                 200                 205

Phe Met Gly Asp Ala Gly Ser Thr Leu Ile Gly Phe Thr Ile Ile Trp
    210                 215                 220

Ile Leu Leu Leu Ser Thr Gln Gly Lys Gly His Pro Met Asn Pro Val
225                 230                 235                 240

Thr Ala Leu Trp Ile Ile Ala Ile Pro Leu Ile Asp Met Val Ala Ile
                245                 250                 255

Ile Tyr Arg Arg Val Arg Lys Gly Lys Ser Pro Phe Arg Pro Asp Arg
            260                 265                 270

Leu His Val His His Leu Met Val Arg Ala Gly Leu Thr Ser Arg Gln
        275                 280                 285

Ala Phe Leu Leu Ile Thr Phe Val Ser Ala Val Cys Ala Thr Ile Gly
    290                 295                 300

Ile Leu Gly Glu Val Tyr Tyr Val Asn Glu Trp Ala Met Phe Val Gly
305                 310                 315                 320

Phe Phe Ile Leu Phe Phe Leu Tyr Val Tyr Ser Ile Thr His Ala Trp
                325                 330                 335

Arg Ile Thr Arg Trp Val Arg Arg Met Lys Arg Arg Ala Lys Arg Leu
```

Lys Lys Ala
    355

<210> SEQ ID NO 4
<211> LENGTH: 1065
<212> TYPE: DNA
<213> ORGANISM: Haemophilus influenzae

<400> SEQUENCE: 4

```
atgctgagta ttttgttac ttttcttggc gcgtttttaa cattgattgt gatgcgacca      60
cttgccaatt ggattggatt agtcgataaa ccaaactatc gtaaacgtca tcaaggcaca     120
attccactaa tcgtggcgc atcgcttttt gttggtaatc tttgctatta tctgatggaa     180
tgggatcaac ttcgattacc gtatctttat ttgttcagta ttttgtttt attggcgatt     240
gggattttag atgatcgctt tgatattagc ccttttttaa gagcaggcat tcaagcaata    300
ttggcgattt taatgatcga tcttgggaat atttatcttg atcatcttgg tcaaatttta    360
gggcctttcc aattaacgct tggttcaatt ggtttgatta ttaccgtctt tgccactatt    420
gcgattatta atgcctttaa tatgattgat ggtattgatg gattgcttgg gggactctct    480
tgtgtttctt ttgcggcgat tggtatttta atgtatcgag atgggcaaat ggatatggcg    540
cattggagtt ttgctttaat cgtatcgatt ttaccttatt tgatgctcaa tctagggatt    600
ccatttggac caaaatataa ggtgtttatg ggggatgccg ggagtacatt aattggcttt    660
accattattt ggattttgtt attaagtacg caaggaaaag ggcatcctat gaatccagta    720
accgcacttt ggattattgc gattcctttg attgatatgg ttgcgattat ttatcgccgt    780
gtacgtaaag gtaaaagccc attccgtcca gatcgtttac atgttcatca tttaatggta    840
agagcgggtt taacatcaag acaagccttt ttattgatta cgtttgtttc tgcagtttgt    900
gcaactatcg gtattttagg ggaagtttat tatgtgaatg agtgggcgat gtttgttggc    960
ttttcatttt tattttttcct ttatgtctat tcaattacgc atgcatggcg aattacccgt   1020
tgggtaagaa gaatgaaacg tcgtgccaaa cggttgaaga aagca                   1065
```

<210> SEQ ID NO 5
<211> LENGTH: 18
<212> TYPE: DNA
<213> ORGANISM: Artificial Sequence
<220> FEATURE:
<223> OTHER INFORMATION: A synthetic primer

<400> SEQUENCE: 5

```
gctggttata tcggttct                                                    18
```

<210> SEQ ID NO 6
<211> LENGTH: 19
<212> TYPE: DNA
<213> ORGANISM: Artificial Sequence
<220> FEATURE:
<223> OTHER INFORMATION: A synthetic primer

<400> SEQUENCE: 6

```
gatcagaata gcaagtcgc                                                   19
```

<210> SEQ ID NO 7
<211> LENGTH: 26
<212> TYPE: DNA
<213> ORGANISM: Artificial Sequence
<220> FEATURE:

-continued

```
<223> OTHER INFORMATION: A synthetic primer

<400> SEQUENCE: 7
cctacgatat gaataggatc attacg                                   26

<210> SEQ ID NO 8
<211> LENGTH: 24
<212> TYPE: DNA
<213> ORGANISM: Artificial Sequence
<220> FEATURE:
<223> OTHER INFORMATION: A synthetic primer

<400> SEQUENCE: 8
cagtagctaa ccccaataca aaag                                     24
```